(12) United States Patent
Rao

(10) Patent No.: US 11,110,098 B2
(45) Date of Patent: Sep. 7, 2021

(54) METHODS AND MEDICAMENTS FOR THE TREATMENT OF RENAL CELL CARCINOMA

(71) Applicant: University of Kansas, Lawrence, KS (US)

(72) Inventor: Reena Rao, Overland Park, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 16/614,997

(22) PCT Filed: Jun. 6, 2018

(86) PCT No.: PCT/US2018/036326
§ 371 (c)(1),
(2) Date: Nov. 19, 2019

(87) PCT Pub. No.: WO2018/226875
PCT Pub. Date: Dec. 13, 2018

(65) Prior Publication Data
US 2020/0215075 A1 Jul. 9, 2020

Related U.S. Application Data

(60) Provisional application No. 62/516,549, filed on Jun. 7, 2017.

(51) Int. Cl.
*A61K 31/55* (2006.01)
*A61P 35/00* (2006.01)

(52) U.S. Cl.
CPC .............. *A61K 31/55* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,972,882 A | 10/1999 | Gattone, II | |
| 8,372,830 B2 * | 2/2013 | Liu | A61P 9/00 |
| | | | 514/212.01 |
| 8,883,145 B2 * | 11/2014 | Stagg | A61K 35/00 |
| | | | 424/130.1 |
| 10,376,507 B2 * | 8/2019 | Srinivasan | A61K 31/05 |
| 2019/0076425 A1 * | 3/2019 | Srinivasan | A61K 31/496 |

OTHER PUBLICATIONS

Cucchiari et al., "Juxtaglomerular Cell Tumor: Multicentric Synchronous Disease Associated With Paraneoplastic Syndrome", 2013, Journal of Clinical Oncology, 31(14), pp. e240-e242. (Year: 2013).*
Salahudeen et al., "Tolvaptan in Hospitalized Cancer Patients With Hyponatremia", 2014, Cancer, 120(5), pp. 744-751. (Year: 2014).*
Greef et al., "Medical treatment of renal cancer: new horizons", 2016, British Journal of Cancer, 115(5), pp. 505-516. (doi.org/10.1038/bjc.2016.230) (Year: 2016).*
Sinha et al., "Inhibition of Vasopressin Type 2 Receptor Signaling Suppresses Tumor Growth in Renal-Cell Carcinoma", Oct. 2017, J. Am. Soc. Nephrol., vol. 28, p. 463, Abstract No. FR-PO247, Meeting Info: Kidney Week 2017. New Orleans, LA, United States. Oct. 31, 2017-Nov. 5, 2017. (Year: 2017).*
Sinha et al., "Targeting the vasopressin type-2 receptor for renal cell carcinoma therapy", 2020, Oncogene, 39(6), pp. 1231-1245. (doi.org/10.1038/s41388-019-1059-0) (Year: 2020).*
Gattone II et al. "Novel Therapies for Polycystic Kidney Disease" J Genet Syndr Gene Ther S4:004, Oct. 29, 2011 (doi: 10.4172/2157-7412.S4-001); 9 pages.
International Search Report issued in PCT Application: PCT/US2018/036236, dated Aug. 27, 2018.
Notification Concerning Transmittal of International Preliminary Report on Patentability issued on PCT PCT/US2018/036326 dated Mar. 12, 2020.

* cited by examiner

*Primary Examiner* — My-Chau T. Tran
(74) *Attorney, Agent, or Firm* — Foley & Lardner LLP

(57) ABSTRACT

The present disclosure is directed, among other things, to the surprising and unexpected efficacy provided by select $V_2R$ antagonists in significantly reducing the cell proliferation levels of clear cell renal cell carcinoma. Thus, the present disclosure provides methods, uses, and medicaments that include such select $V_2R$ antagonists for utility in treating clear cell renal cell carcinoma.

20 Claims, 20 Drawing Sheets

METHODS AND MEDICAMENTS FOR THE TREATMENT OF RENAL CELL CARCINOMA

CROSS-REFERENCE TO RELATED APPLICATIONS

This application is a U.S. national phase application under 35 U.S.C. § 371 of International Application No. PCT/US2018/036326, filed on Jun. 6, 2018, which claims the benefit of and priority to U.S. Provisional Patent Application No. 62/516,549, filed Jun. 7, 2017, the entire disclosures of which are hereby incorporated by reference in their entireties for any and all purposes.

U.S. GOVERNMENT RIGHTS

This invention was made with government support under DK083525 awarded by the National Institutes of Health. The government has certain rights in the invention.

BACKGROUND

Renal cell carcinoma (RCC) accounts for 90% of all kidney cancers and is among the 10 most common cancers worldwide. Clear cell RCC (CCRCC) and papillary cell RCC represent 70-75% cases of all RCC. There is a need for therapeutic methods of treating CCRCC, including suppressing tumor growth.

SUMMARY

In an aspect, a method of treating a subject suffering from clear cell renal cell carcinoma is provided. The method includes administering to the subject an effective amount of a compound selected from OPC31260, OPC41061, a pharmaceutically acceptable salt of either thereof, or a mixture of any two or more thereof, where the effective amount is an amount effective for treating clear cell renal cell carcinoma.

In a related aspect, use of OPC31260, OPC41061, a pharmaceutically acceptable salt of either thereof, or a mixture thereof for treating a subject suffering from clear cell renal cell carcinoma is provided. In a further related aspect, use of OPC31260, OPC41061, a pharmaceutically acceptable salt of either thereof, or a mixture thereof in the manufacture of a medicament for the treatment of clear cell renal cell carcinoma in a subject is provided.

DETAILED DESCRIPTION

Figure 1:
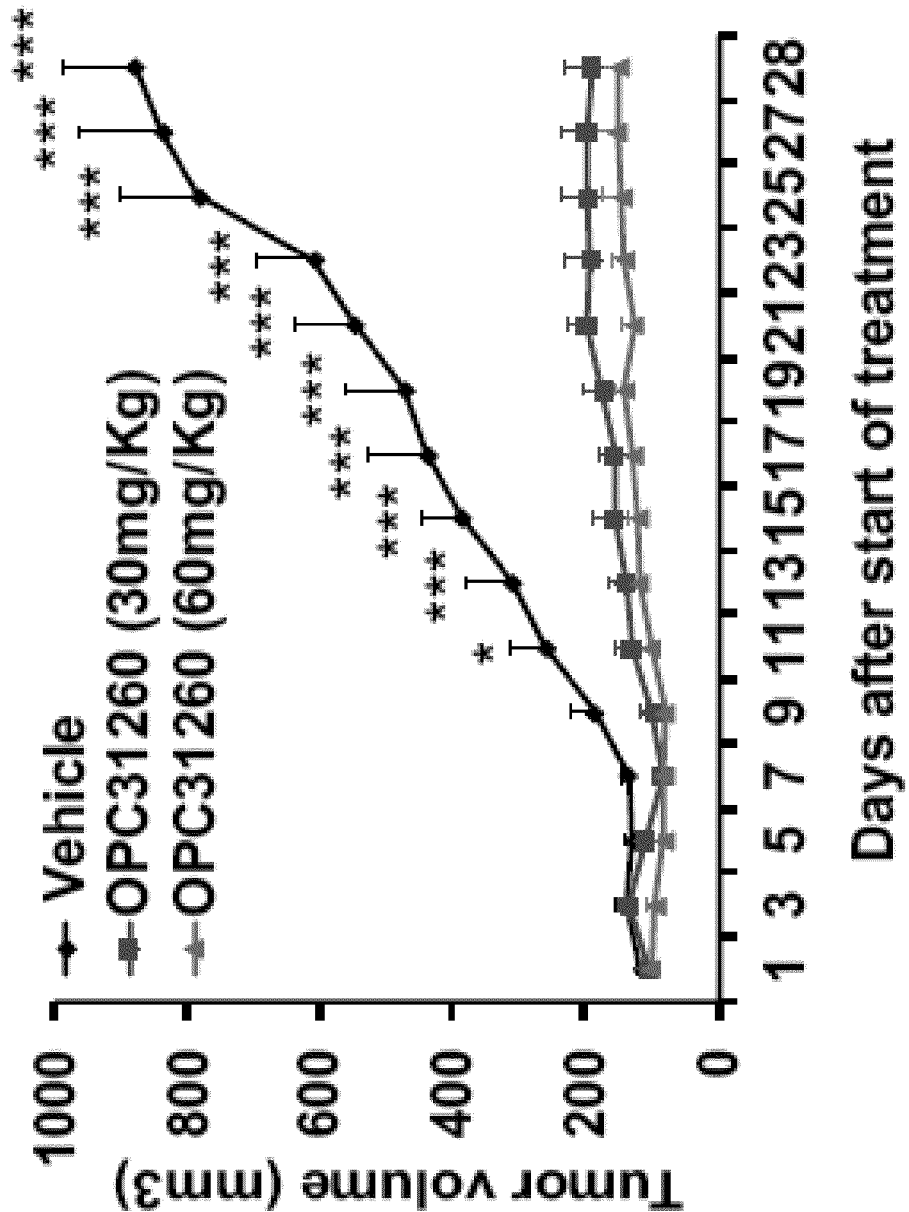
FIG. 1 provides the tumor volume of Nu/Nu mice that had been inoculated subcutaneously with Caki-1 cells 10 days prior to the study versus daily intraperitoneal injections with vehicle or OPC31260 (30 and 60 mg/Kg) for 28 days (*P<0.05, ***P<0.001 vs OPC31260 (30 and 60 mg/Kg)), according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$ and $^{35}S$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$) ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

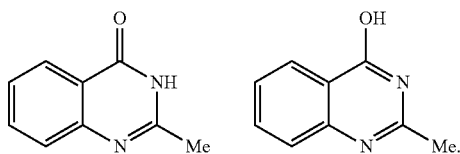 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

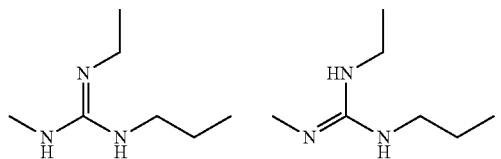

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which the present technology pertains.

"Treating" within the context of the instant technology is well-understood by a person of ordinary skill in the art. To the extent the term may be unclear, the term "treating" means alleviation, in whole or in part, of symptoms, for example the symptoms of a clear cell renal cell carcinoma, associated with a disorder or disease, or slowing, inhibition or halting of further progression or worsening of those symptoms, or prevention or prophylaxis of the disease or disorder in a subject at risk for developing the disease or disorder.

The Present Technology

Neuropeptide hormones and their receptors are often abnormally involved in the oncogenic transformation process in various cancers, and are emerging targets for cancer therapy[14]. The antidiuretic hormone, arginine vasopressin (AVP) is a neuropeptide produced mainly by the hypothalamus. To elicit its action, AVP binds to its type-1 and type-2 G-protein coupled receptors ($V_{1a}R$, $V_{1b}R$ and $V_2R$). $V_2R$ is expressed in the kidneys (normally restricted in kidneys to the thick ascending limb, connecting tubules, and renal collecting ducts) where it helps to regulate water and salt homeostasis' and in endothelial cells, where it controls hemostasis[2].

However, ectopic expression and activity of AVP and its receptors have been reported to suppress cell proliferation, metastasis and angiogenesis in breast, pancreatic, colorectal and gastrointestinal cancers, and small cell lung carcinoma[3-6]. Moreover, the $V_2R$ agonist desmopressin (dDAVP) and its analog [$V^4Q^5$]dDAVP have shown angiostatic, anti-proliferative and/or anti-metastatic effects in breast, lung, and colorectal cancers[7-9].

Abnormal $V_2R$ expression has also been reported in renal cell carcinoma (RCC) cell lines of human origin (Caki-2 and A498 cells)—where, in contrast to the above-mentioned studies, $V_2R$ activation by dDAVP increased proliferation of these RCC cell lines in vitro[10]. While the $V_2R$ antagonist satavaptan (also referred to as SR121463B) abolished dDAVP-induced proliferation of RCC cell lines in vitro, satavaptan treatment did not reduce time-dependent increase in cell proliferation of these RCC cell lines, instead only countering further increased proliferation of Caki-2 by a $V_2R$ agonist—i.e., Caki-2 proliferation remained at baseline levels.[3] RCC, the most common cancer of the kidneys accounts for 90% of all kidney cancers and 2-3% of all malignant diseases[11]. RCCs occur in 8 major subtypes[12], of which clear cell and papillary-cell RCC represent 70-75% of the cases of RCC[13] and are thought to originate from proximal tubules[13], which normally express $V_1R$.

To determine if $V_2R$ was expressed as well as active in human clear cell RCC tumors (i.e., not just merely expressed in certain cell lines), the Applicant engaged in studies to measure its expression and canonical cell signaling, including intracellular cAMP levels, and ERK and CREB activation, per methods described further herein. $V_2R$ expression was detected that was associated with tumor cell membranes and $V_2R$ mRNA in RCC tumor biopsy samples (data not shown). An overall increase in expression of pERK1/2 (Thr202/Tyr204), ERK1/2, pCREB (Ser133) and CREB as well as intracellular cAMP levels was observed in RCC tumors as compared to normal kidney tissue (data not shown). Thus, $V_2Rs$ are not only abnormally expressed in clear cell RCC tumors, but are also active.

The present disclosure is directed, among other things, to the surprising and unexpected efficacy provided by select $V_2R$ antagonists in reducing the baseline cell proliferation levels of clear cell RCC (CCRCC). Thus, the present disclosure provides uses and medicaments including such select $V_2R$ antagonists for utility in treating clear cell RCC. As illustrated in the working examples, the $V_2R$ antagonist OPC31260 reduces cell viability and clonogenicity in 786-O and Caki-1 human clear cell RCC cell lines by causing cell cycle arrest at the G2/M phase. Furthermore, OPC31260 and OPC41061 (commonly referred to as tolvaptan; another $V_2R$ antagonist), significantly suppressed clear cell RCC tumor growth in a mouse xenograft model. Treatment of the mice with either OPC31260 or tolvaptan reduced cell proliferation and angiogenesis in CCRCC tumors, and increased apoptosis in such tumors.

Thus, in an aspect, a method of treating a subject suffering from clear cell renal cell carcinoma is provided. The method includes administering to the subject an effective amount of a compound selected from OPC31260, OPC41061, a pharmaceutically acceptable salt of either thereof, or a mixture of any two or more thereof (collectively, "compounds of the present technology" or "the compound"), where the effective amount is an amount effective for treating clear cell renal cell carcinoma. In any embodiment herein, administering one or more compounds of the present technology may include parenteral administration, subcutaneous administration, intravenous administration, intraperitoneal administration, intramuscular administration, and/or oral administration. The clear cell renal cell carcinoma of any embodiment herein may include one or more of VHL mutant CCRCC and VHL wildtype CCRCC. In any embodiment herein, the method may include administering one or more compounds of the present technology to the subject from about 1 to about 7 times per week (such as about 1, about 2, about 3, about 4, about 5, about 6, about 7, or any range including and/or in between any two of these values). In any embodiment herein, the method may include administering the compound to the subject daily. Such daily administration in any embodiment herein may include administering one or more compounds of the present technology to the subject about once a day, about twice a day, about three times a day, about four times a day, or any range including and/or in between any two of these values, or any range greater than any one of these values.

OPC31260 (also known as mozavaptan; 5-(dimethylamino)-1-[4-(2-methylbenzamido)benzoyl]-2,3,4,5-tetrahydro-1H-benzazepine) is a $V_2R$ antagonist represented by the following structure:

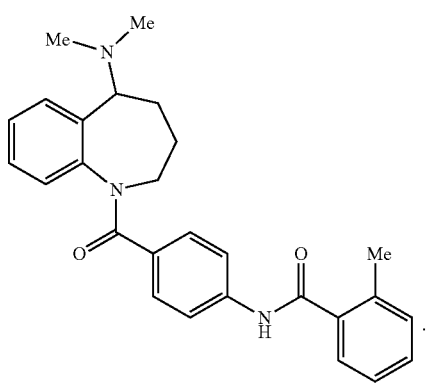 [SMILES: Cc1ccccc1C(=O)Nc1ccc(C(=O)N2CCCC(N(C)C)c3ccccc32)cc1]

OPC41061 (also known as tolvaptan; N-[4-[(7-chloro-2,3,4,5-tetrahydro-5-hydroxy-1H-1-benzazepin-1-yl)carbonyl]-3-methylphenyl]-2-methylbenzamide) is a $V_2R$ antagonist represented by the following structure:

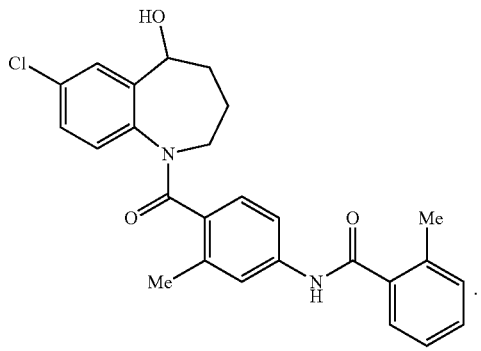 [SMILES: Cc1ccccc1C(=O)Nc1ccc(C(=O)N2CCCC(O)c3cc(Cl)ccc32)c(C)c1]

As an example, in any embodiment herein the method may include administering an effective amount of OPC31260 or a pharmaceutically acceptable salt thereof to the subject. As another example, in any embodiment herein the method may include administering an effective amount of OPC41061 or a pharmaceutically acceptable salt thereof to the subject.

The method of any embodiment herein may include administering a composition where the composition includes OPC31260, OPC41061, a pharmaceutically acceptable salt of either thereof, or a mixture of any two or more thereof, in addition to a pharmaceutically acceptable carrier; the method of any embodiment herein may include administering a medicament that includes OPC31260, OPC41061, a pharmaceutically acceptable salt of either thereof, or a mixture of any two or more thereof.

Thus, present technology also provides compositions (e.g., pharmaceutical compositions/medicaments) that include OPC31260, OPC41061, a pharmaceutically acceptable salt of either thereof, or a mixture of any two or more thereof, and a pharmaceutically acceptable carrier (such as one or more excipients or fillers). The compositions may be used in any embodiments of the methods, treatments, uses, etc., described herein. The pharmaceutical composition may include an effective amount of OPC31260, OPC41061, a pharmaceutically acceptable salt of either thereof, or a mixture of any two or more thereof.

In any embodiment herein, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of a clear cell RCC. Another example of an effective amount includes amounts or dosages that yield acceptable toxicity and bioavailability levels for therapeutic (pharmaceutical) use including, but not limited to, a clear cell RCC. Yet another example of an effective amount includes amounts or dosages that are capable of reducing symptoms associated with a clear cell RCC, such as, for example, hematuria, kidney pain, weight loss, lack of appetite, fever, fatigue, anemia, night sweats, hypercalcemia and/or high blood pressure. For each of the indicated symptoms described herein, test subjects will exhibit a 10%, 20%, 30%, 50% or greater reduction, up to a 75-90%, or 95% or greater, reduction, in one or more symptom(s) caused by, or associated with a clear cell RCC, compared to placebo-treated or other suitable control subjects. A further example of an effective amount includes amounts or dosages that are capable of reducing the volume, weight, or density of a clear cell RCC tumor. The effective amount may be from about 0.01 μg to about 100 mg of the compound per gram of the composition, and preferably from about 0.1 μg to about 500 μg of the compound per gram of the composition. As used herein, a "subject" or "patient" is a mammal, such as a human, a bovine, an equine, a canine, a feline, a simian, a porcine, an ovine, an avian, or a rodent (e.g., mouse). Typically the subject is a human, and, preferably, a human suffering from or suspected of suffering from a clear cell RCC. The term "subject" and "patient" can be used interchangeably.

In any of the embodiments of the present technology described herein, the pharmaceutical composition may be packaged in unit dosage form. The unit dosage form is effective in treating prostate cancer or breast cancer. Generally, a unit dosage including one or more compounds of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg.

Dosage/administration of a compound of the present technology may also vary from 0.01 mg/kg to 200 mg/kg or, preferably, from 0.1 mg/kg to 10 mg/kg. For example, the dosage may be about 0.01 mg to about 150 mg of one or more compounds of the present technology per kilogram of the subject; in any embodiment of a method or use of the present technology, it may include administering to the subject about 0.01 mg/kg to about 150 mg/kg of one or more compounds of the present technology. Thus, the dosage/administration of OPC31260, OPC41061, a pharmaceutically acceptable salt of either thereof, or a mixture of any two or more thereof, may be about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 12 mg/kg, about 14 mg/kg, about 16 mg/kg, about 18 mg/kg, about 20 mg/kg, about 22 mg/kg, about 24 mg/kg, about 26 mg/kg, about 28 mg/kg, about 30 mg/kg, about 32 mg/kg, about 34 mg/kg, about 36 mg/kg, about 38 mg/kg, about 40 mg/kg, about 42 mg/kg, about 44 mg/kg, about 46 mg/kg, about 48 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 110 mg/kg, about 120 mg/kg, about 130 mg/kg, about 140 mg/kg, about 150 mg/kg, or any range including and/or in between any two of these values. Specific dosages may be adjusted depending on, for example, age, protocol, condition, sex, extent of disease, excretion rate, contraindications, concomitant therapies and the like.

Those skilled in the art are readily able to determine an effective amount and/or dosage, for example, by simply administering a compound of the present technology, for example, OPC31260, OPC41061, a pharmaceutically acceptable salt of either thereof, or a mixture of any two or more thereof, to a patient in increasing amounts until, for example, the volume, weight, or density of a tumor is reduced relative to the volume, weight, or density before administration of the compounds; or until the rate of increase in volume, weight, or density of the tumor is reduced. For clear cell RCC, the volume, weight, or density of the tumor may be assessed using in vivo imaging and/or by taking a tumor sample from the subject and observing the target of interest therein.

Effectiveness of the compounds of the present technology in treating clear cell renal cell carcinoma may also be demonstrated by a decrease in the symptoms of clear cell renal cell carcinoma, such as, for example, hematuria, kidney pain, weight loss, lack of appetite, fever, fatigue, anemia, night sweats, hypercalcemia, and/or high blood pressure. For each of the indicated symptoms described herein, test subjects will exhibit a 10%, 20%, 30%, 50% or greater reduction, up to a 75-90%, or 95% or greater, reduction, in one or more symptom(s) caused by, or associated with a clear cell RCC, compared to placebo-treated or other suitable control subjects.

In any embodiment herein, the method may further include administering water to the patient. Water may be administered to assist with clearance of waste in patients reduced urine osmolality, as is known for current treatment protocols with, e.g., OPC41061. Water may be administered orally, intravenously, etc.

In any embodiment herein, the method may further include administering to the subject one or more conventional therapeutic agents useful in the treatment of a clear cell RCC. In any embodiment herein, the method of the present technology may include c administering, either sequentially or in combination with the OPC31260, OPC41061, a pharmaceutically acceptable salt of either thereof, or a mixture of any two or more thereof, an effective amount of one or more conventional therapeutic agents.

Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

For example, in any embodiment herein of the present technology, OPC31260, OPC41061, a pharmaceutically acceptable salt of either thereof, or a mixture of any two or more thereof, may be included in a liquid formulation (such as an injectable formulation, an intravenous formulation, a subcutaneous formulation, and/or an oral liquid formulation) that includes about 0.1 mg/mL (i.e., 0.1 mg compound per 1 mL liquid formulation) to about 50 mg/mL of the OPC31260, OPC41061, a pharmaceutically acceptable salt of either thereof, or a mixture of any two or more thereof. Thus, the liquid formulation may include the OPC31260, OPC41061, a pharmaceutically acceptable salt of either thereof, or a mixture of any two or more thereof, at about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 12 mg/mL, about 14 mg/mL, about 16 mg/mL, about 18 mg/mL, about 20 mg/mL, about 22 mg/mL, about 24 mg/mL, about 26 mg/mL, about 28 mg/mL, about 30 mg/mL, about 32 mg/mL, about 34 mg/mL, about 36 mg/mL, about 38 mg/mL, about 40 mg/mL, about 42 mg/mL, about 44 mg/mL, about 46 mg/mL, about 48 mg/mL, about 50 mg/mL, or any range including and/or in between any two of these values.

As another example, in any embodiment herein of the present technology, OPC31260, OPC41061, a pharmaceutically acceptable salt of either thereof, or a mixture of any two or more thereof, may be included in a solid oral formulation (such as a tablet, pill, or capsule) that includes about 0.1 mg to about 100 mg of the OPC31260, OPC41061, a pharmaceutically acceptable salt of either thereof, or a mixture of any two or more thereof. Thus, the solid oral formulation may include the OPC31260, OPC41061, a pharmaceutically acceptable salt of either thereof, or a mixture of any two or more thereof, at about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 12 mg, about 14 mg, about 16 mg, about 18 mg, about 20 mg, about 22 mg, about 24 mg, about 26 mg, about 28 mg, about 30 mg, about 32 mg, about 34 mg, about 36 mg, about 38 mg, about 40 mg, about 42 mg, about 44 mg, about 46 mg, about 48 mg, about 50 mg, about 52 mg, about 54 mg, about 56 mg, about 58 mg, about 60 mg, about 62 mg, about 64 mg, about 66 mg, about 68 mg, about 70 mg, about 72 mg, about 74 mg, about 76 mg, about 78 mg, about 80 mg, about 92 mg, about 94 mg, about 96 mg, about 98 mg, about 100 mg, or any range including and/or in between any two of these values.

The pharmaceutical compositions may be prepared by mixing OPC31260, OPC41061, a pharmaceutically acceptable salt of either thereof, a mixture of any two or more thereof, or solvates thereof, with one or more pharmaceutically acceptable carriers, excipients, binders, diluents or the like to prevent and treat disorders associated with a clear cell RCC. The compounds of the present technology may be used to prepare formulations and medicaments that treat prostate cancer and/or breast cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing at least one of compound of the present technology, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, and/or emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers, and combinations of any two or more thereof. The carriers and stabilizers may vary and may include one or more of nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. For example, in any embodiment of the present technology disclosed herein, the pharmaceutically acceptable carrier may include one or more of a polyethylene glycol, a polyethylene glycol fatty acid monoester, a polyethoxylene sorbitan monoester, or a combination of any two or more thereof.

Dosage forms for the topical (including buccal and sublingual) or transdermal administration of compounds of the present technology include powders, sprays, ointments, pastes, creams, lotions, gels, solutions, and patches. Compounds of the present technology may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also include, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology. For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

EXAMPLES

Exemplary Studies of the Effect of Select $V_2R$ Antagonists and Agonists on CCRCC Materials and Methods
 Drugs and Reagents:
 Tolvaptan (7-chloro-5-hydroxy-1-[2-methyl-4-(2-methylbenzoylamino) benzoyl]-2,3,4,5-tetrahydro-1H-1-benzazepine), OPC31260 hydrochloride (5-(dimethylamino)-1-[4-(2-methylbenzamido)benzoyl]-2,3,4,5-tetrahydro-1H-benzazepine hydrochloride), and the $V_2R$ agonist dDAVP (1-desamino-8-d-arginine vasopressin) were purchased from Sigma Millipore (St. Louis, Mo.). Primary antibodies for pCREB (Cat. No. 9198S), CREB (Cat. No. 9197S), p-histone 3 (Cat. No. 9701S), Ki-67 (Cat. No. 9449S), BRDU (Cat. No. 5292Si), pERK1/2 (Cat. No. 9101 S), and ERK (Cat. No. SC-94) were procured from Cell Signaling Technology (Danvers, Calif.). c-Myc (Cat. No. SC-764), VEGF (Cat. No. SC-7269) and GAPDH (Cat. No. SC-47724) from Santa Cruz Biotechnology (Santa Cruz, Calif.). Anti-vasopressin V2 receptor antibody (Cat. No. V5514) was purchased from Sigma Millipore (St. Louis, Mo.). CD31 antibody (Cat. No. ab28364) was purchased from Abcam (Cambridge, Mass., U.S.A). Secondary antibodies from Dako (Carpinteria, Calif.) and ECL reagent from Perkin Elmer (Waltham, Mass., USA) were used. Immunohistochemistry was performed using Streptavidin HRP conjugated anti-mouse or anti-rabbit using a DAB kit (Vector laboratories, CA). For immunofluorescence, goat anti-rabbit IgG fluor and goat anti-mouse IgG Texas red (Invitrogen, NY, USA) were used.

Cell Culture and Human Tumor Tissue:

786-O, Caki-1, ACHN human RCC cells, and HK-2 Human renal proximal tubular cells were obtained from American Type Culture Collection (ATCC) and maintained in DMEM/F12 medium supplemented with 10% FBS, penicillin (100 U/ml), and streptomycin (100 µg/ml). Primary cultures of human autosomal dominant polycystic kidney disease (ADPKD) cells were obtained from the PKD Biomarkers and Biomaterials Core in the Jared Grantham Kidney Institute at the University of Kansas Medical Center (KUMC). De-identified human RCC tumor tissues from surgically removed samples from 10 patients, each of whom had pathologically proven clear cell RCC, and control normal kidney tissue were obtained from the University of Kansas Cancer Center's Biospecimen Repository Core Facility between August 2005 and October 2010. The study protocol was approved by the Institutional Review Board (IRB).

In Vivo Xenograft Study:

Female Athymic Nude-Foxn1$^{nu}$ mice (Nu/Nu mice), 7-8 weeks old and weighing ~25 g were procured from Envigo/Harlan. All animal studies were carried out according to the protocols approved by the University of Kansas Medical Center Institutional Animal Care and Use Committee. Mice were subcutaneously injected on the right flank region with $1\times10^6$ Caki-1 cells in 100 µl of DMEM medium. One week after injection, palpable tumors appeared and tumor volume was measured with calipers following the formula, Tumor volume=(length×width)/2. Once the tumor volume reached ~80-100 mm$^3$, mice were randomized into sub-groups based on the tumor volume. Animals were administered vehicle, OPC31260 (30 mg/Kg BWt.), OPC31260 (60 mg/Kg BWt) or dDAVP (1 µg/Kg BWt.) and vehicle (saline) by daily intraperitoneal injection, (60 mg/Kg BWt) or dDAVP (1 µg/Kg BWt.) and vehicle (saline) by daily intraperitoneal injection, or tolvaptan (120 mg/Kg BWt. in 1% aqueous solution of hydroxypropyl methylcellulose-dose derived from previous study[31]) or vehicle by daily oral gavage for 28 days. Body weights and tumor volumes were measured every alternate day. At the end of the study, mice were injected with BRDU (100 mg/Kg BWt. by IP) 90 minutes before sacrifice. Tumors were harvested, photographed and weighed. Tumors were flash frozen or paraffin embedded for further analysis.

Cell Viability:

MTT assays were performed to measure cell viability. Briefly, exponentially growing 786-O and Caki-1 cells were seeded in 96 well plates. After 24 h, cells were incubated with different doses of OPC31260 for 48 h. The cells were then incubated in MTT solution (5 mg/mL) for 2 h, following which the MTT solution was removed and the intracellular purple formazan was solubilized in DMSO and quantified by spectrophotometry at 570 nM.

Clonogenic Assay:

786-O and Caki-1 cells were plated at very low density (1,000 cells/well) in six-well plates. After 16 h, cells were treated with different doses of OPC31260 and incubated for 48 h. Cells were washed and grown for 10 days until visible colonies formed. Colonies were fixed with 4% paraformaldehyde in PBS, stained with 0.25% crystal violet in 25% methanol, washed, air-dried and photographed. Crystal violet was dissolved in sodium citrate buffer (0.1M, 50% ethanol, pH 4.2) and absorbance was recorded at 590 nM.

Cell Cycle Analysis:

786-O and Caki-1 cells were incubated for 24 h with 0, 1, 5, 10, 25 or 50 µM of OPC31260, and stained with propidium iodide for analysis by flow cytometry. Cells were rinsed with PBS and trypsinized, and washed twice with PBS. Single-cell suspensions were fixed using pre-chilled 70% ethanol overnight, and subsequently permeabilized with PBS containing 0.1% Triton X-100, 1 mg/ml propidium iodide (Sigma-Aldrich) and 2 mg/ml DNase-free RNase at room temperature. Flow cytometry was done with a FACS Calibur analyzer (Becton Dickinson, Mountain, View, Calif.), capturing 10,000 events for each sample. Results were analyzed with ModFit LT™ software (Verity Software House, Topsham, Me.).

Detection of Apoptosis/Necrosis Using Annexin V-FITC/PI Staining:

Annexin V-FITC/PI staining was performed for quantification of apoptosis and necrotic cell death using FITC AnnexinV apoptosis detection kit I. Green FITC dye stains apoptotic cells whereas propidium iodide stains necrotic cells with red fluorescence. RCC cells were incubated with OPC31260 for 24 h and washed in cold PBS and resuspended in calcium containing binding buffer (10 mM HEPES, 140 mM NaCl, 5 mM $CaCl_2$; pH 7.4) at a concentration of $1\times10^6$ cells/ml and stained for 15 min, with 5 µl Annexin V-FITC and 5 µl PI at 1 µg/ml (Cell signaling kit, USA). 10,000 cells were analyzed at an excitation wavelength of 488 nm and emission wavelengths of 530 nm for FITC fluorescence and 610 nm for PI fluorescence. The percentages of viable (Annexin V−PI−), early apoptotic (Annexin V+PI−), late apoptotic/necrotic (Annexin V+PI+) and necrotic cells (Annexin V-PI+) were evaluated with the CellQuestPro® software (Becton, Dickinson, Heidelberg, Germany).

Measurement of cAMP:

A cAMP Enzyme Immunoassay Kit (Direct) from Sigma-Aldrich was used. Human RCC tumors were ground to a fine powder under liquid nitrogen and homogenized in 10 volumes of ice cold 0.1% HCl, centrifuged at 600 g, and cAMP levels were measured following the manufacturer's protocols.

Real-Time PCR:

RT-PCR using RNA isolated from whole tissue samples, and cultured cells was carried out as described before and $V_2R$ expression was determined in human renal cancer cells and tumor tissues. The primer sequences of human $V_2R$ used were (F: GTC GCA CCT ATG TCA CCT GG and R: ACT GGC ATG AAT CTC CCG GA).

Immunoblotting:

Tumors from mouse xenografts and cultured 786-O and Caki-1 cells were homogenized in SDS Laemmli buffer and loaded onto 10% SDS-polyacrylamide agarose gel electrophoresis gels, transferred to nitrocellulose membranes and blocked with 5% milk in TBST[32]. Membranes were probed with primary antibody followed by wash and horseradish peroxidase secondary antibody application.

Immunostaining:

Tumor tissues were fixed overnight in 4% paraformaldehyde, dehydrated in a graded alcohol series, and embedded in paraffin for histological analysis as previously described[26]. Slides with 5 µm tissue sections were heated in a steamer for 20 min in citrate buffer (pH 6.0) to unmask antigens. Slides were further blocked with 10% goat serum (Invitrogen) and then incubated overnight with primary antibody ($V_2R$, CD31, BRDU, Ki67 and p-H3). After washing the slides with PBST, slides were incubated with appropriate fluorescence-labeled secondary antibody (Invitrogen) and streptavidin HRP conjugated (Invitrogen) secondary antibody for immunoflurorescence and immunohistochemistry, respectively. Slides were also incubated in 4',6-diamidino-2-phenylindole to visualize nuclei. For immunofluorescence staining, slides were mounted with Fluoromount G (Southern Biotech). For immunohistochemistry, slides were developed with DAB (Vector Laboratories) and counterstained with Harris haematoxylin, dehydrated, and mounted with Permount (Fisher Scientific, Waltham, Mass.). All images were captured using a Nikon 80i microscope (Tokyo, Japan) at the KUMC Imaging Center.

TUNEL Assay for Apoptosis:

TUNEL assays were performed to check apoptosis using the in situ Cell Death Detection Kit (Roche Applied Science, Indianapolis, Ind.). Briefly, slides with 5-µm tumor sections were treated to a TUNEL reaction mixture containing terminal deoxynucleotidyl transferase and nucleotides, including tetramethylrhodamine-labeled dUTP. Both Dapi stained and TUNEL-positive nuclei were counted as described for proliferating cell nuclear antigen. All images were captured using a Nikon 80i microscope (Tokyo, Japan) in the KUMC Imaging Center.

Figure 9:
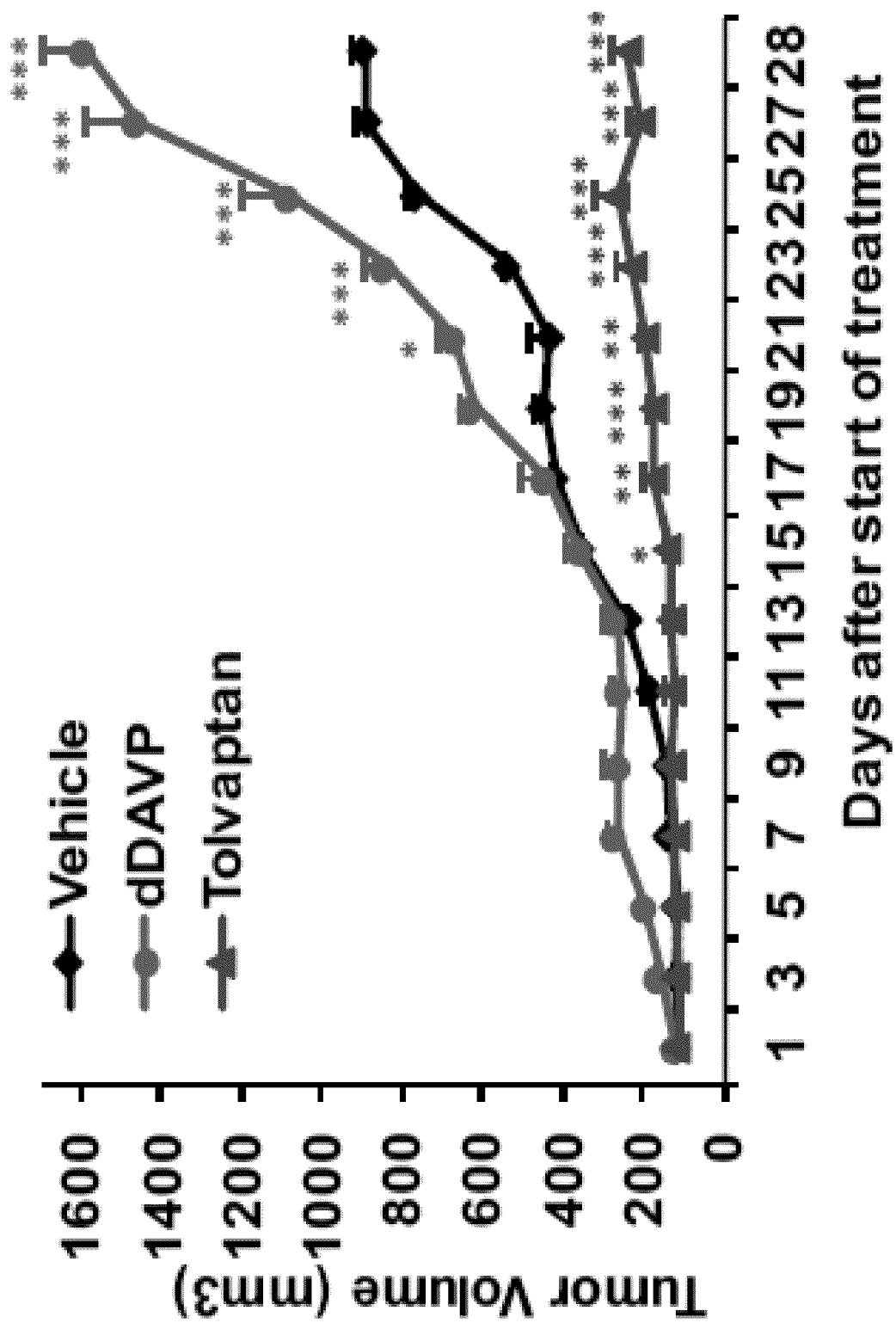
FIG. 9 provides the tumor volume of Nu/Nu mice that had been inoculated subcutaneously with Caki-1 cells 10 days prior to the study versus daily intraperitoneal injections with vehicle, tolvaptan (120 mg/Kg), or dDAVP (1 µg/Kg) for 28 days, according to the working examples.

Statistical Analysis: Comparisons Between Treatment Groups were Performed by Two-tailed unpaired t-test with Welch's correction. In FIG. 9, two way repeated measures of ANOVA followed by the Bonferroni test was carried out. Comparisons of multiple points were made using analysis of variance (ANOVA) followed by the Bonferroni test. $P<0.05$ was considered significant. Data were expressed as Mean±SEM for mouse studies and Mean±SD for cell culture studies.

Representative Results

Figure 2:
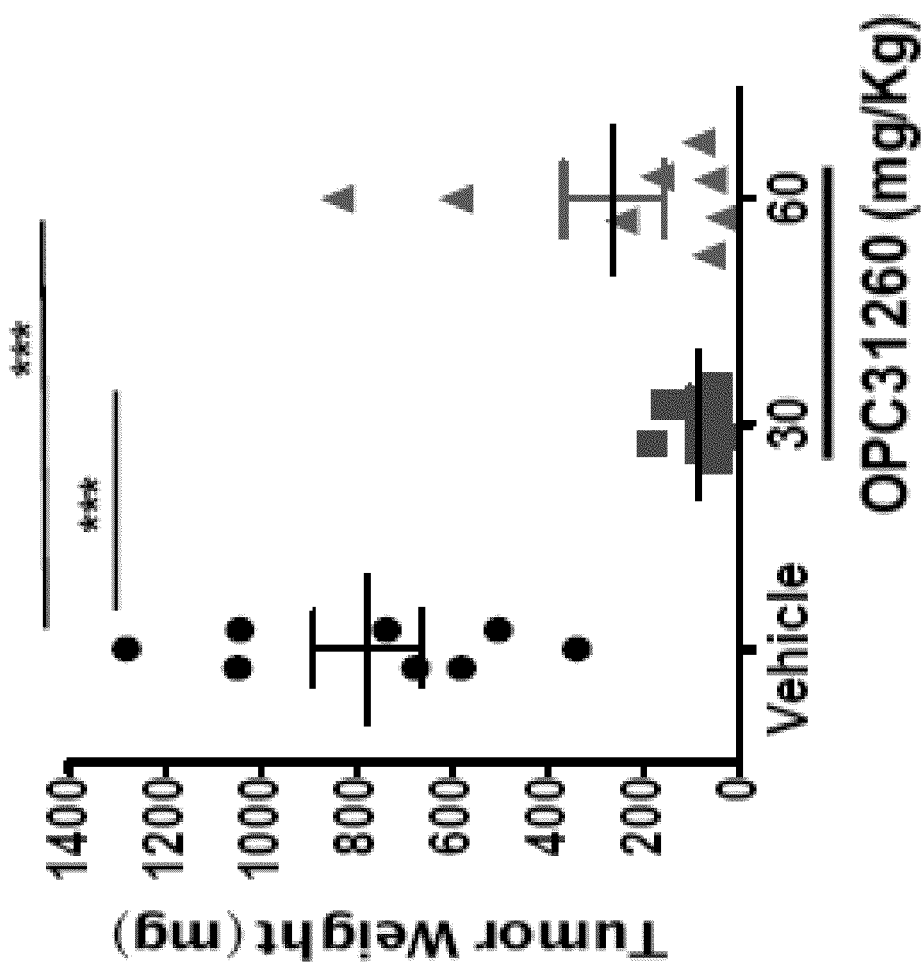
FIG. 2 provides the tumor weights at sacrifice of the mice from the same study that produced the data of FIG. 1, according to the working examples.

To determine the effect of $V_2R$ inhibition on RCC tumor development, OPC31260, a $V_2R$ antagonist was tested in a murine xenograft model. For the studies, Caki-1 cells which expressed $V_2R$ were implanted subcutaneously in nude mice, and 10 days later, when the tumors reached approximately 80-100 mm³, the mice were randomized into three groups for treatment with vehicle, OPC31260 (30 mg/Kg), and OPC31260 (60 mg/Kg) for 28 days by daily intraperitoneal injections. Tumor volume in the vehicle treatment group increased steadily and was 9-fold higher than its baseline values by day 28. However, in the OPC31260 treatment groups, tumor volume failed to show a significant increase (FIG. 1). At sacrifice after 28 days of treatment, the tumors in the OPC31260 treatment groups were significantly smaller than in the vehicle treatment group (FIG. 2). OPC31260 treatment did not significantly change body weight of the mice but reduced urine osmolality in a dose dependent manner, supporting that OPC31260 at these doses caused minimal toxicity and inhibited the $V_2R$ regulated urine concentrating ability in these mice, as expected. These results demonstrate that $V_2R$ inhibition by OPC31260 inhibits CCRCC tumor growth in mice.

Figure 3:
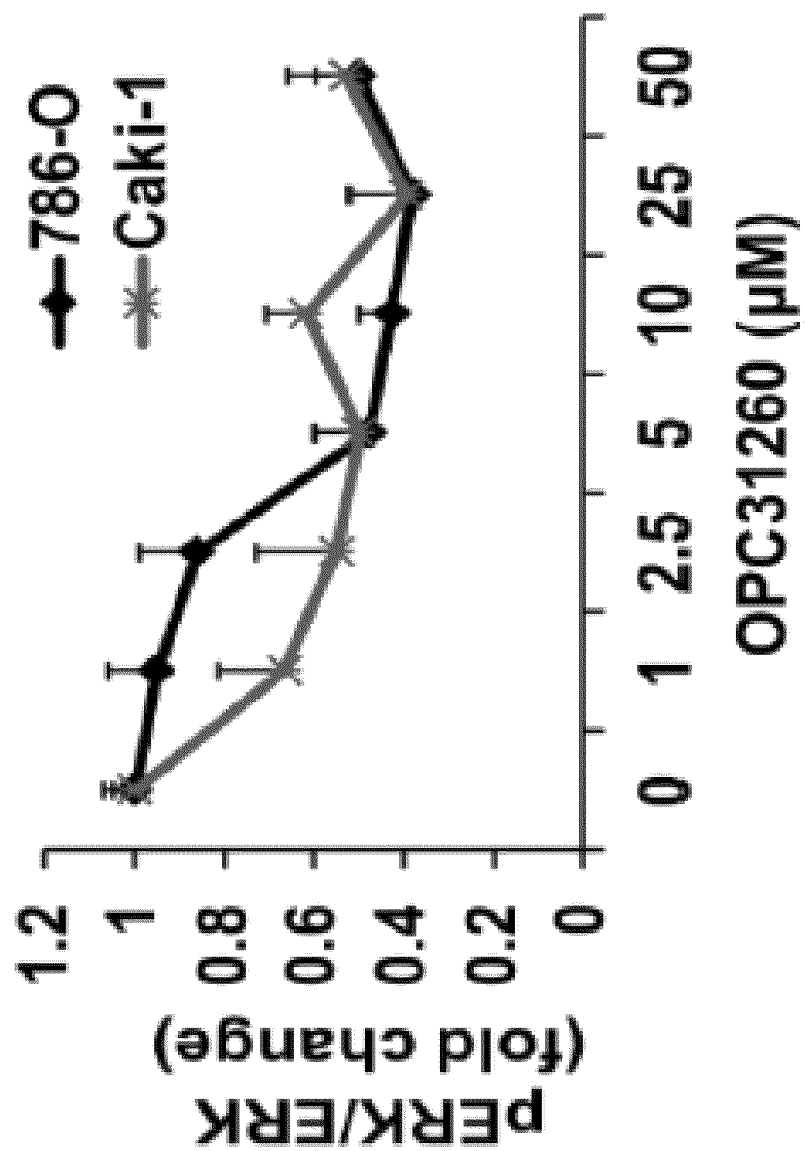
FIG. 3 provides a quantitation of Western blot of cell lysate of OPC31260 treated 786-O (24 h) and Caki-1 cells (48 h) for pERK/ERK relative to GAPDH as a function of OPC31260 dose, according to the working examples.
Figure 4:
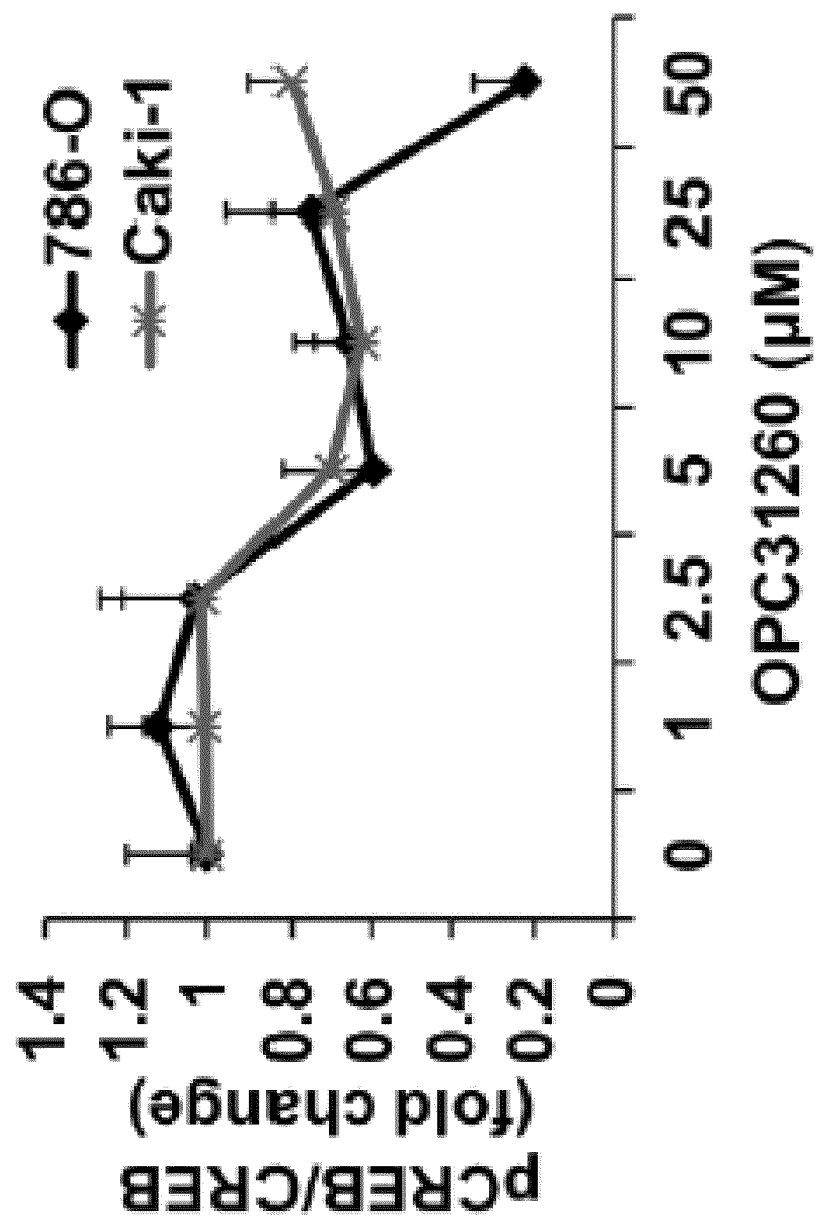
FIG. 4 provides a plot of pCREB/CREB change as a function of OPC31260 dose for OPC31260 treated 786-O (24 h) and Caki-1 cells (48 h), according to the working examples.
Figure 5:
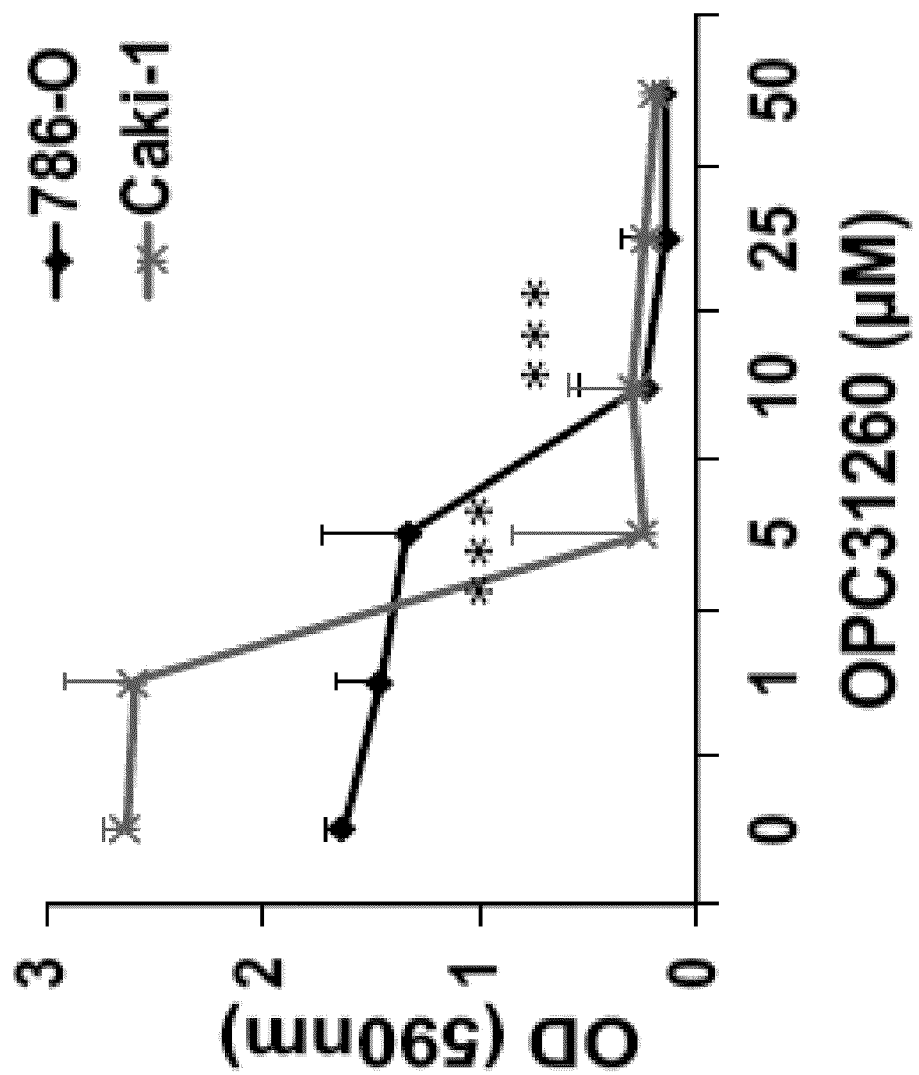
FIG. 5 plots OPC31260 treatment-resistant colony formation of Caki-1 and 786-O cell lines (***P<0.001 vs 0 µM OPC31260, (n=4)), according to the working examples.
Figure 6:
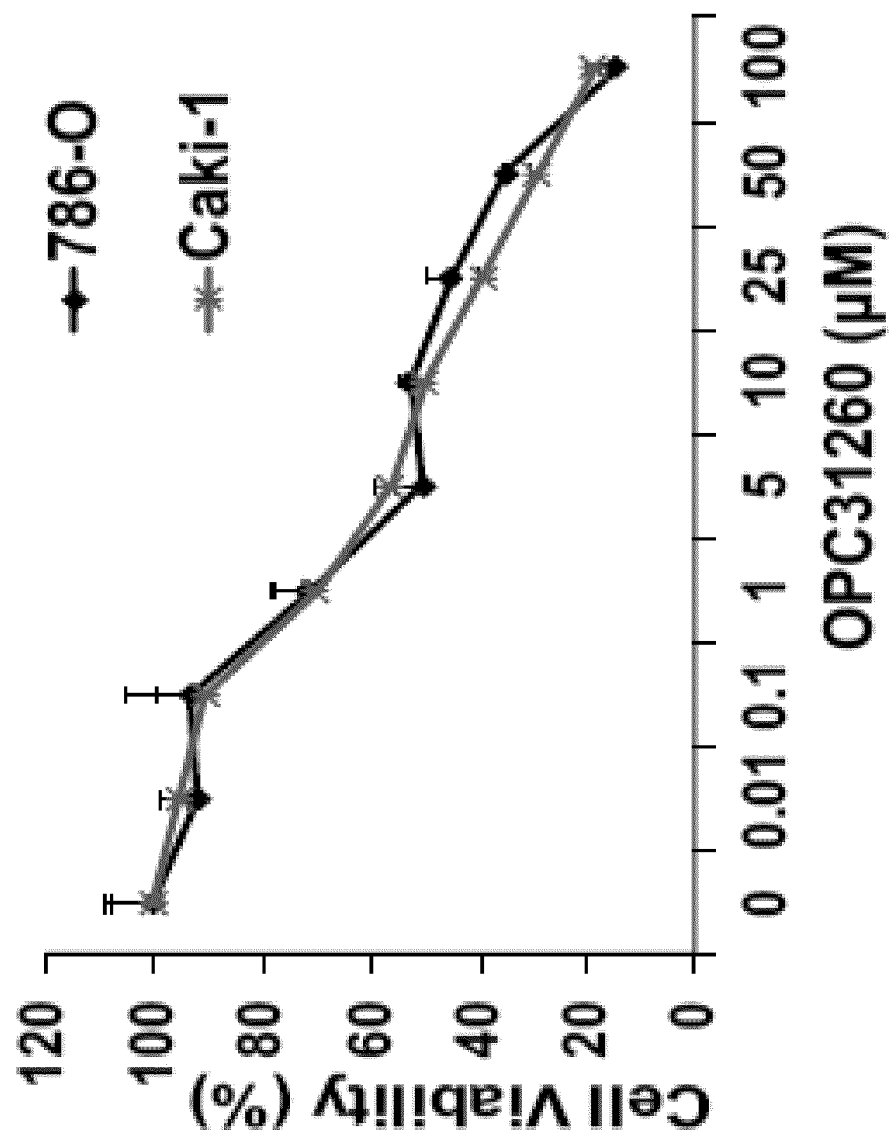
FIG. 6 plots the cell viability versus dosage of 786-O and Caki-1 cells treated with varying amounts of OPC31260 for 48 h as measured by MTT assay, according to the working examples.
Figure 7:
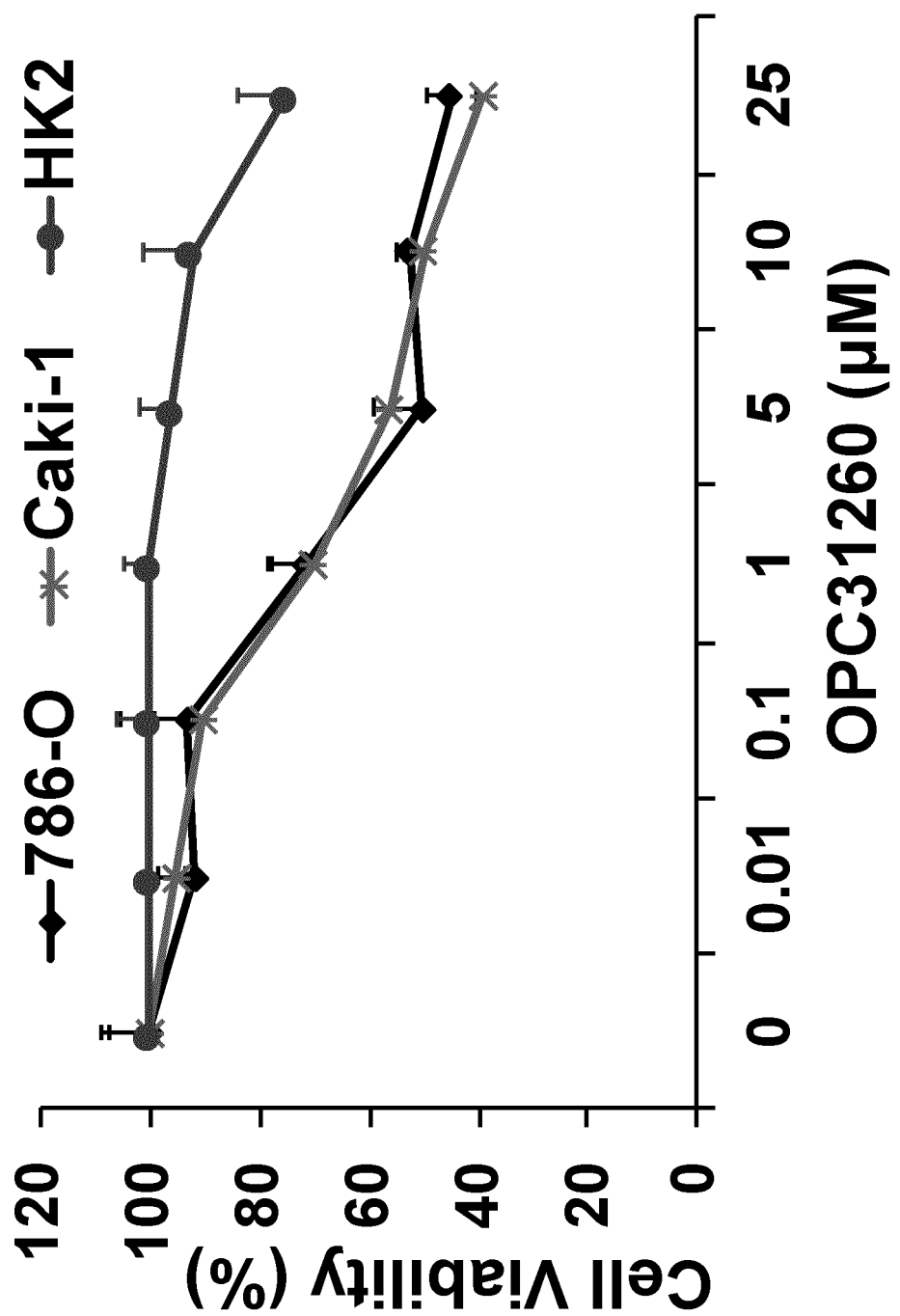
FIG. 7 plots the cell viability versus dosage of 786-O and Caki-1 cells along with normal human proximal tubule cells (HK2) that do not express vasopressin type 2 receptors ($V_2R$) treated with varying amounts of OPC31260 for 48 h as measured by MTT assay, according to the working examples.
Figure 8A:
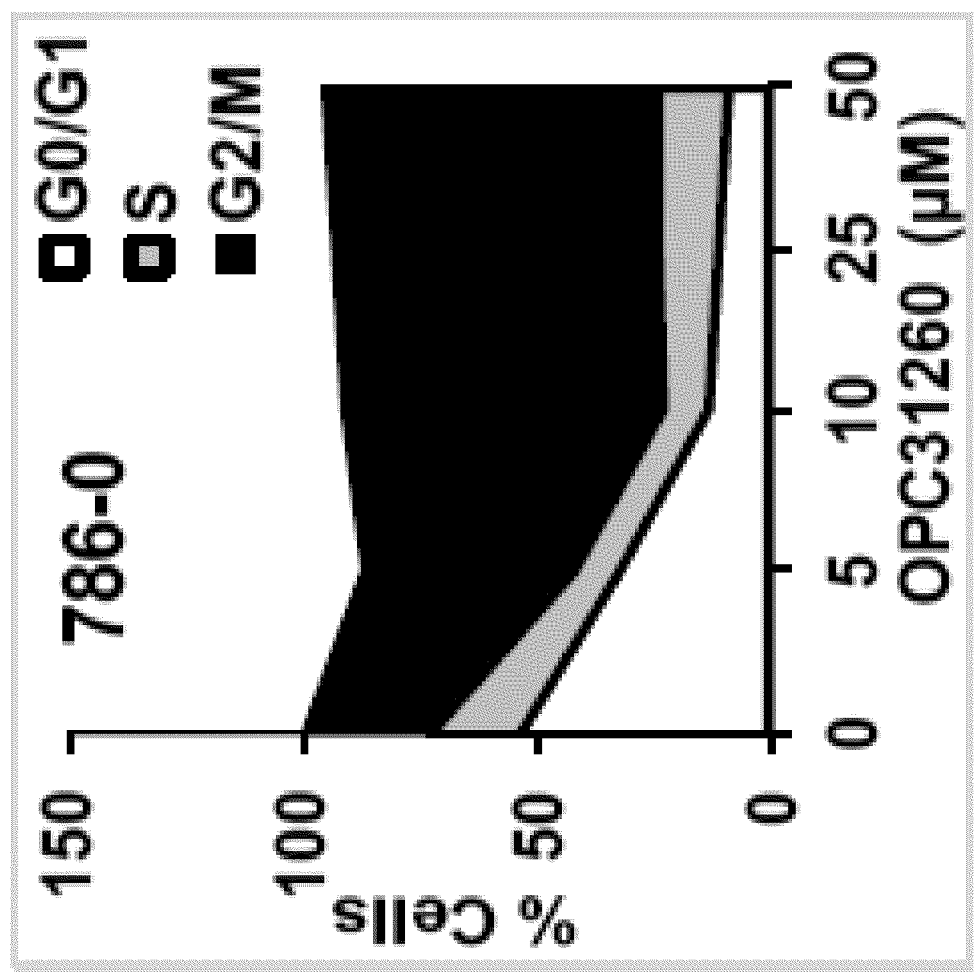
FIGS. 8A-8B quantifies cell cycle stages in 786-O (FIG. 8A) or Caki-1 (FIG. 8B) cells treated with OPC31260 (24 h) as measured by FACS analysis of propidium iodide stained cells, according to the working examples.
Figure 8B:
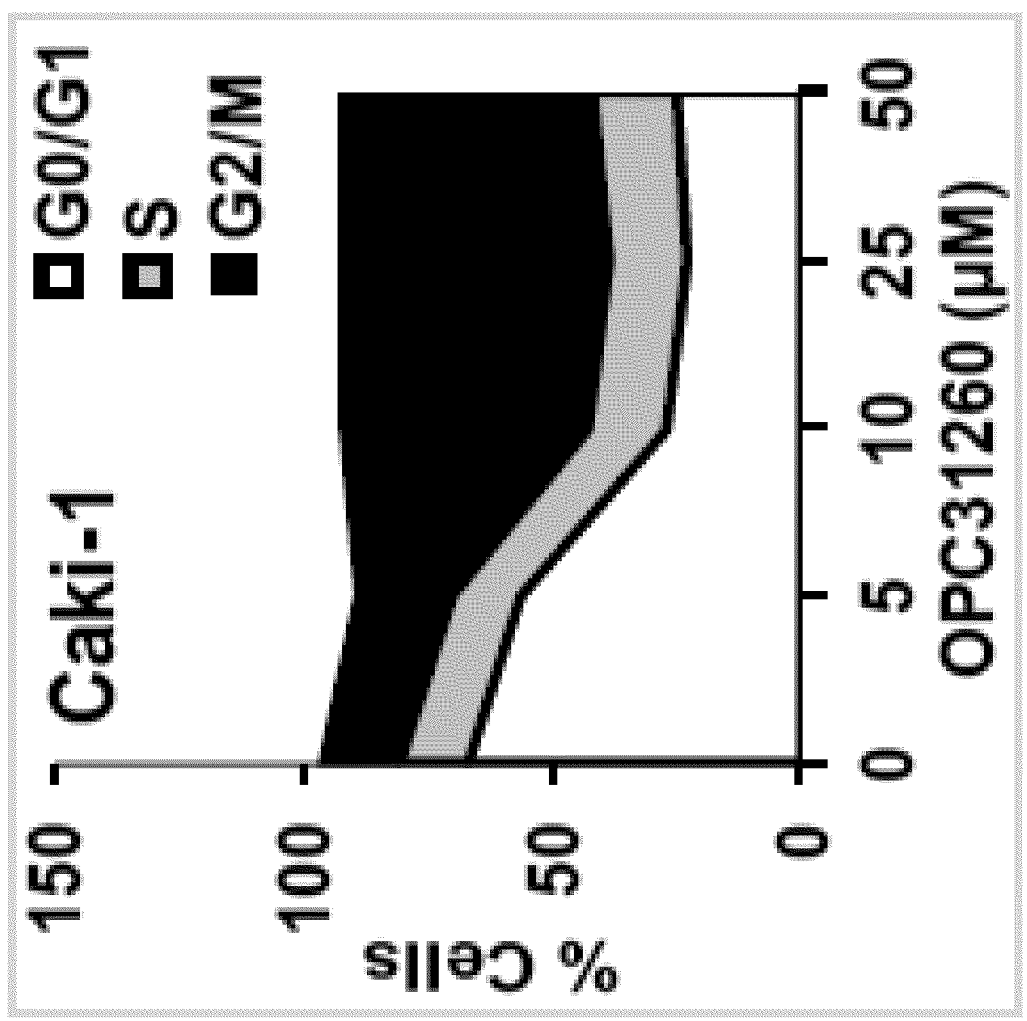
Figure 18A:
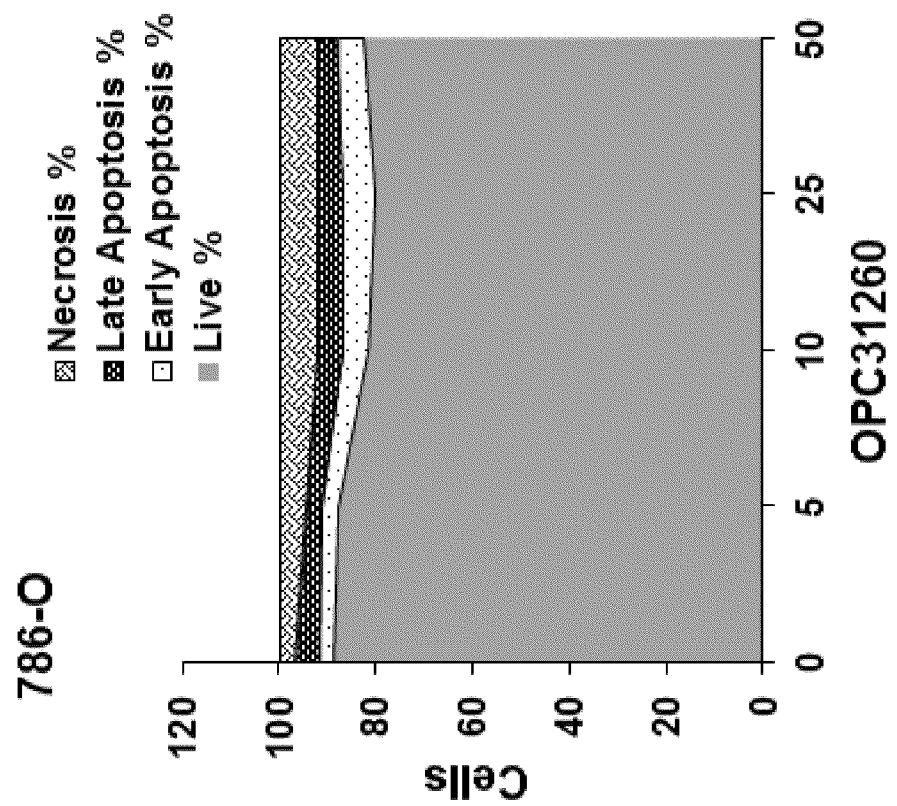
FIGS. 18A-18B provide the percentage of 786-O (FIG. 18A) or Caki-1 (FIG. 18B) cells undergoing apoptotic or necrotic cell death after treatment with OPC31260, according to the working examples.
Figure 18B:
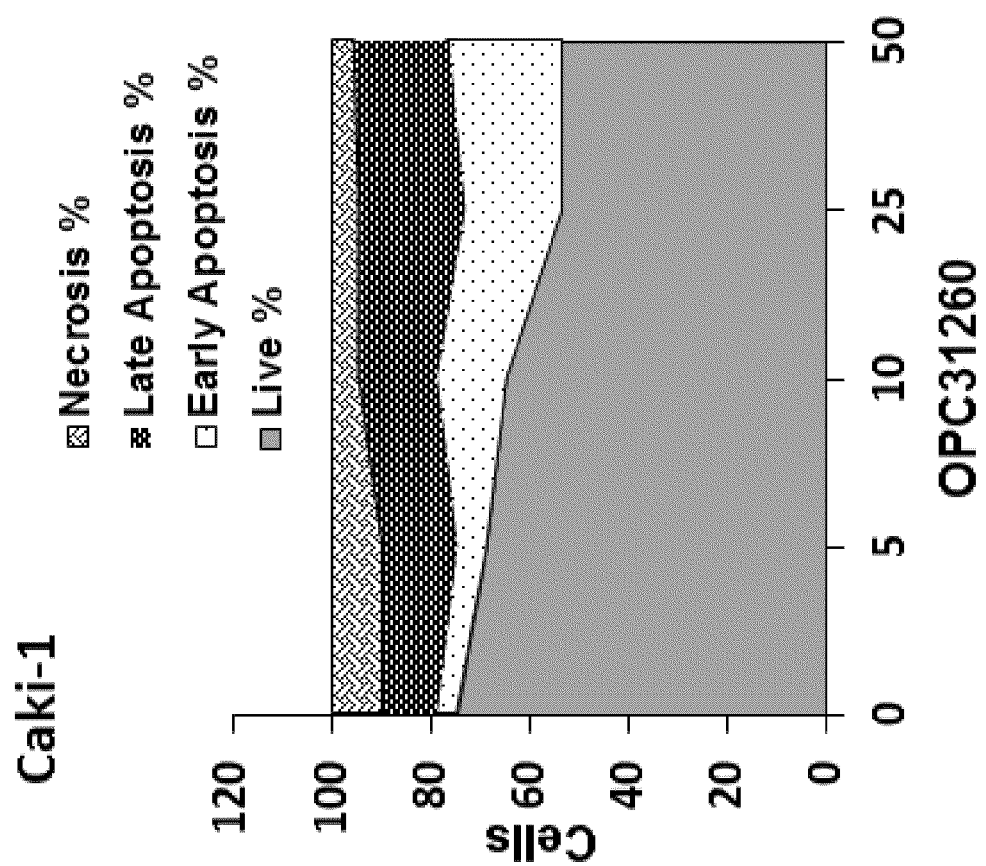

To further determine the role of $V_2R$ in tumor cell survival, proliferation and cell signaling, in vitro studies were carried out. In 786-O and Caki-1 cells, OPC31260 dose-dependently reduced pERK1/2 and pCREB levels (FIGS. 3-4). A significant decline in colony formation was also observed starting at 5 and 10 µM doses of OPC31260 in 786-O and Caki-1 cells respectively (FIG. 5). Moreover, cell viability declined by 50% at 5-10 µM dose of OPC31260 in 786-O and Caki-1 cells (FIGS. 6-7), which was further determined to be due to G2/M cell cycle arrest. 60-70% of cells were found to be in G2/M phase when treated with 10 µM or higher doses of OPC31260 (FIGS. 8A and 8B). OPC31260 treatment also caused an increase in apoptosis in Caki-1 and 786-O cells (FIGS. 18A and 18B). Thus, inhibition of $V_2R$ by OPC31260 in CCRCC cells is cytostatic, reduces clonogenicity, and inhibition of cell proliferation occurs by inducing G2/M cell cycle arrest rather than lytic death.

Tolvaptan (OPC41061), has relatively better oral activity than OPC31260[16]. Tolvaptan shows 29-fold greater selectivity in blocking [³H]AVP binding to human $V_2R$ than V1aR, does not inhibit V1bR, and has no intrinsic $V_2R$ agonistic effect[16]. Importantly, tolvaptan is an FDA approved drug routinely used to treat hyponatremia[17].

Figure 10:
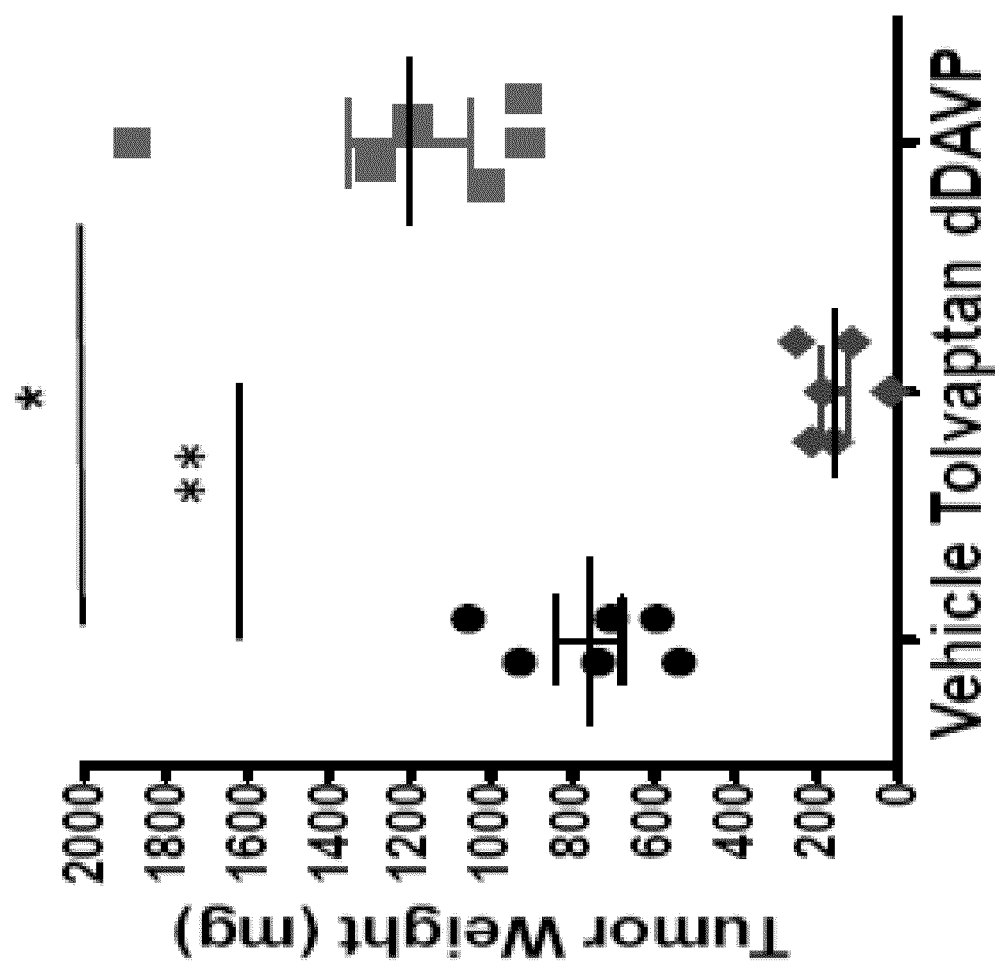
FIG. 10 provides the tumor weights at sacrifice of the mice from the same study that produced the data of FIG. 9, according to the working examples.

The effect of tolvaptan on tumor development in mice was tested as well as the effect of dDAVP, a $V_2R$ agonist. As before, Caki-1 cells were implanted subcutaneously in nude mice, and mice were randomized into three groups: vehicle, tolvaptan (120 mg/Kg, by daily oral gavage) or dDAVP (1 µg/Kg by daily IP injection) for 28 days. Tumor volume in tolvaptan treated mice was significantly reduced compared to vehicle treated mice (FIG. 9), consistent with OPC31260 treatment in the previously described study. Tumor volume in dDAVP group did not increase significantly till day 21, following which, it increased rapidly (FIG. 9). By day 28, the tumor volume in dDAVP group was 16-fold higher than its baseline, and 2-fold higher than vehicle group (FIG. 9). At sacrifice, the tumors in the tolvaptan group were smaller and weighed significantly less as compared to the vehicle group, while in the dDAVP group, average tumor size was larger than in the vehicle group (FIG. 10). Tolvaptan and dDAVP treatment did not significantly change the body weight of the mice, but as with OPC31260 treatment, urine osmolality was significantly reduced by tolvaptan treatment and increased by dDAVP treatment (data not shown), indicating that these compounds were having their expected effects on urine concentrating ability with minimal obvious toxicity.

Figure 11:
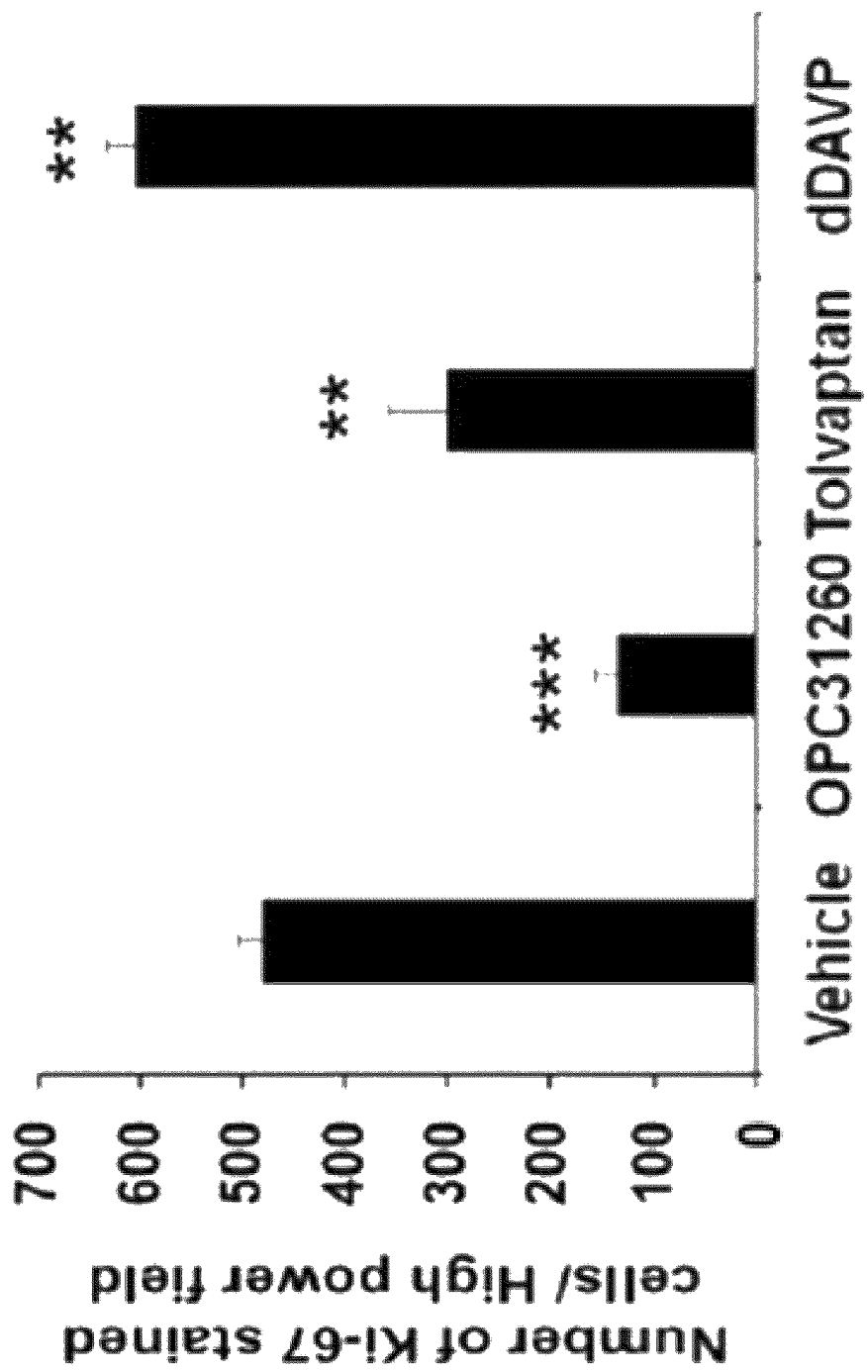
FIG. 11 provides a histogram of Ki-67 stained cells of tumor sections from the same study that produced the data of FIG. 10, where *P<0.05, P<0.01, *P<0.001 vs Vehicle, according to the working examples.
Figure 12:
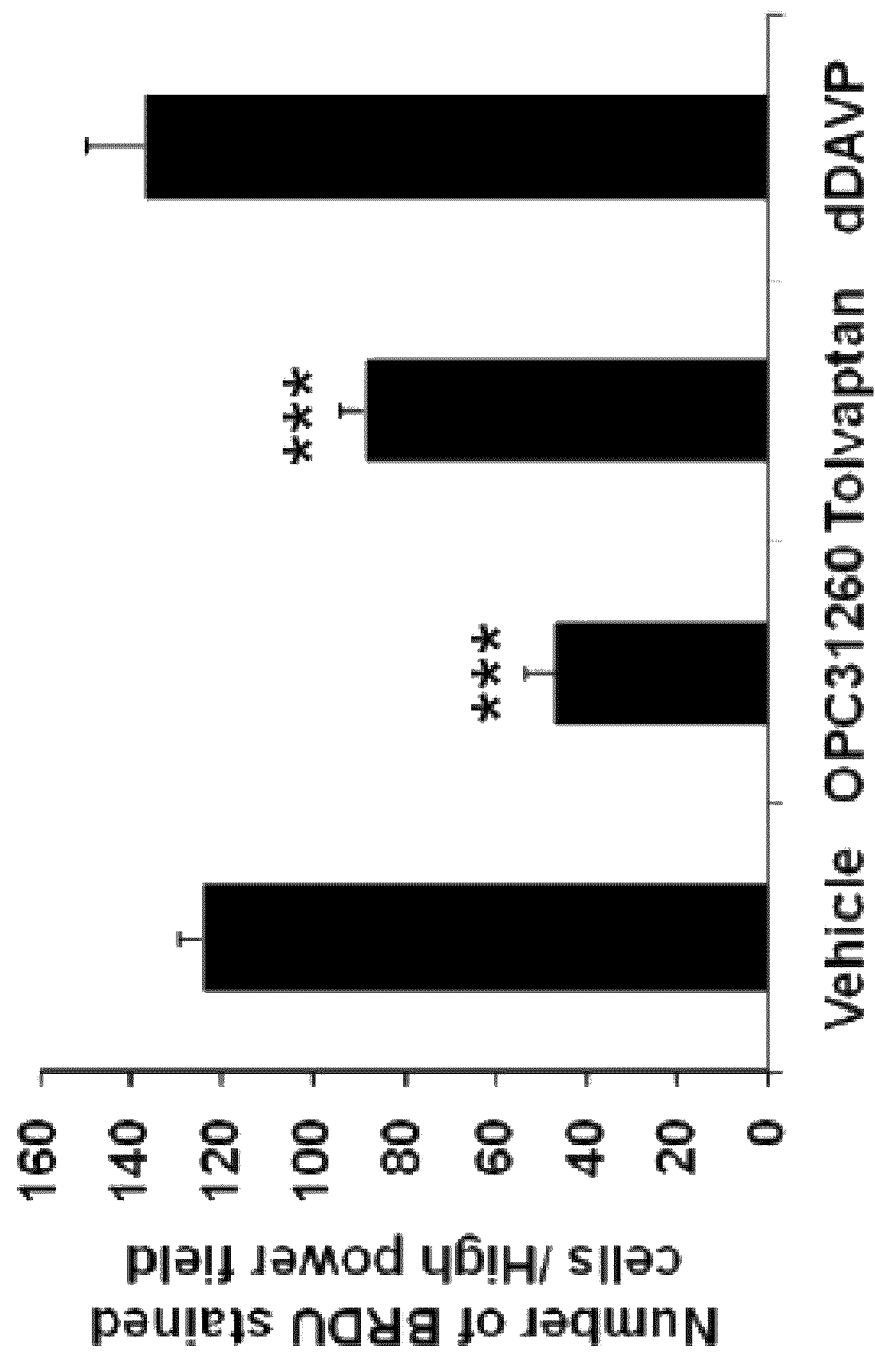
FIG. 12 provides a histogram of BRDU stained cells of tumor sections from the same study that produced the data of FIG. 10, where *P<0.05, P<0.01, *P<0.001 vs Vehicle, according to the working examples.
Figure 13:
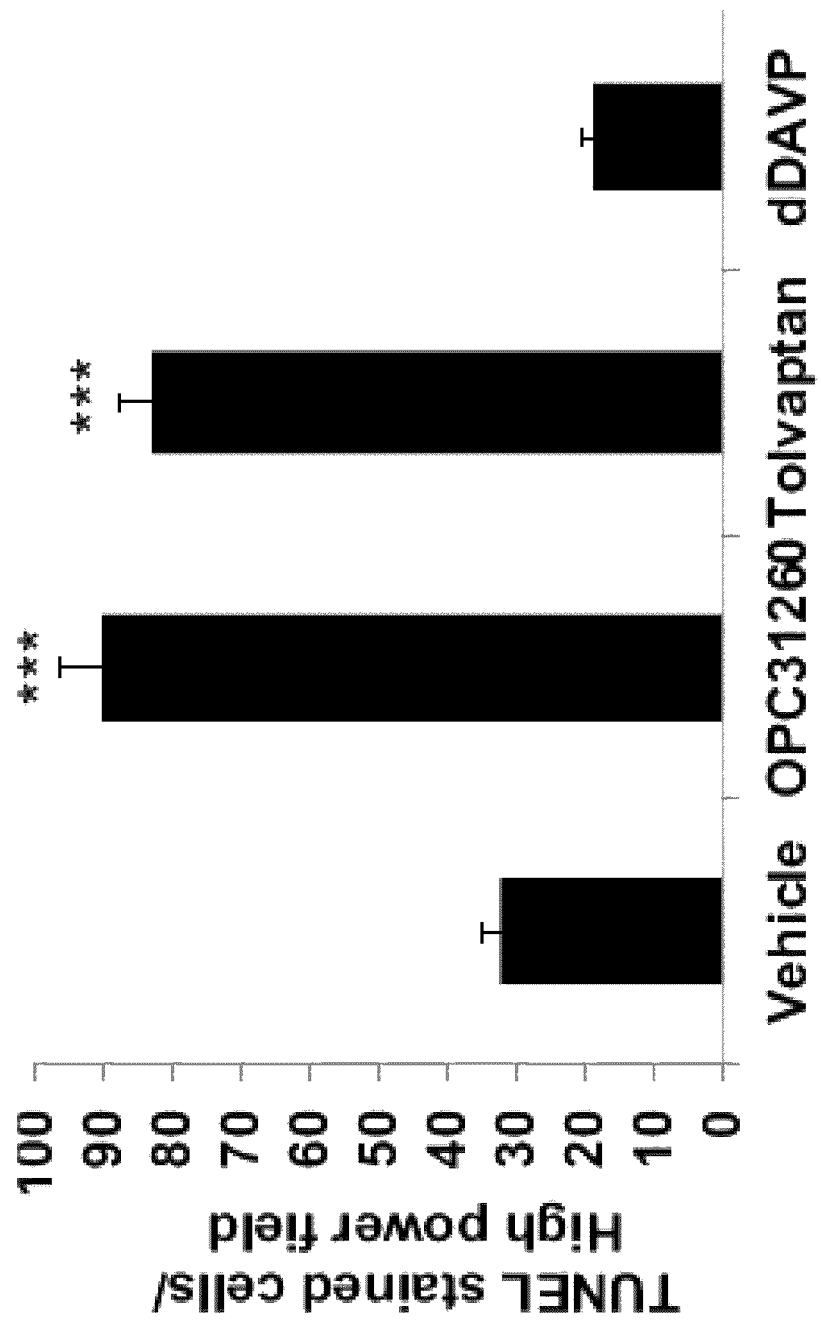
FIG. 13 provides a histogram of TUNEL stained cells of tumor sections from the same study that produced the data of FIG. 10, where *P<0.05, P<0.01, *P<0.001 vs Vehicle, according to the working examples.

Without being bound by theory, the smaller tumor size in the OPC31260 and tolvaptan groups could be attributed to suppressed cell division and increased tumor cell death by apoptosis because their tumors showed significantly reduced Ki-67 and BRDU staining (FIGS. 11-12), and increased TUNEL staining (FIG. 13) compared to vehicle treatment. In contrast, tumors in the dDAVP group showed significant increase in Ki-67 staining (FIG. 11), but no significant change in BRDU incorporation or TUNEL staining compared to vehicle. The effect of tolvaptan on cell proliferation and apoptosis in the examples of RCC study was relatively lower than that of OPC31260, in spite of a higher dose. Without being bound by theory, this could be because tolvaptan was administered orally, compared to OPC31260, and because tolvaptan has a mean absolute bioavailability of only 56% in humans[30].

Figure 14:
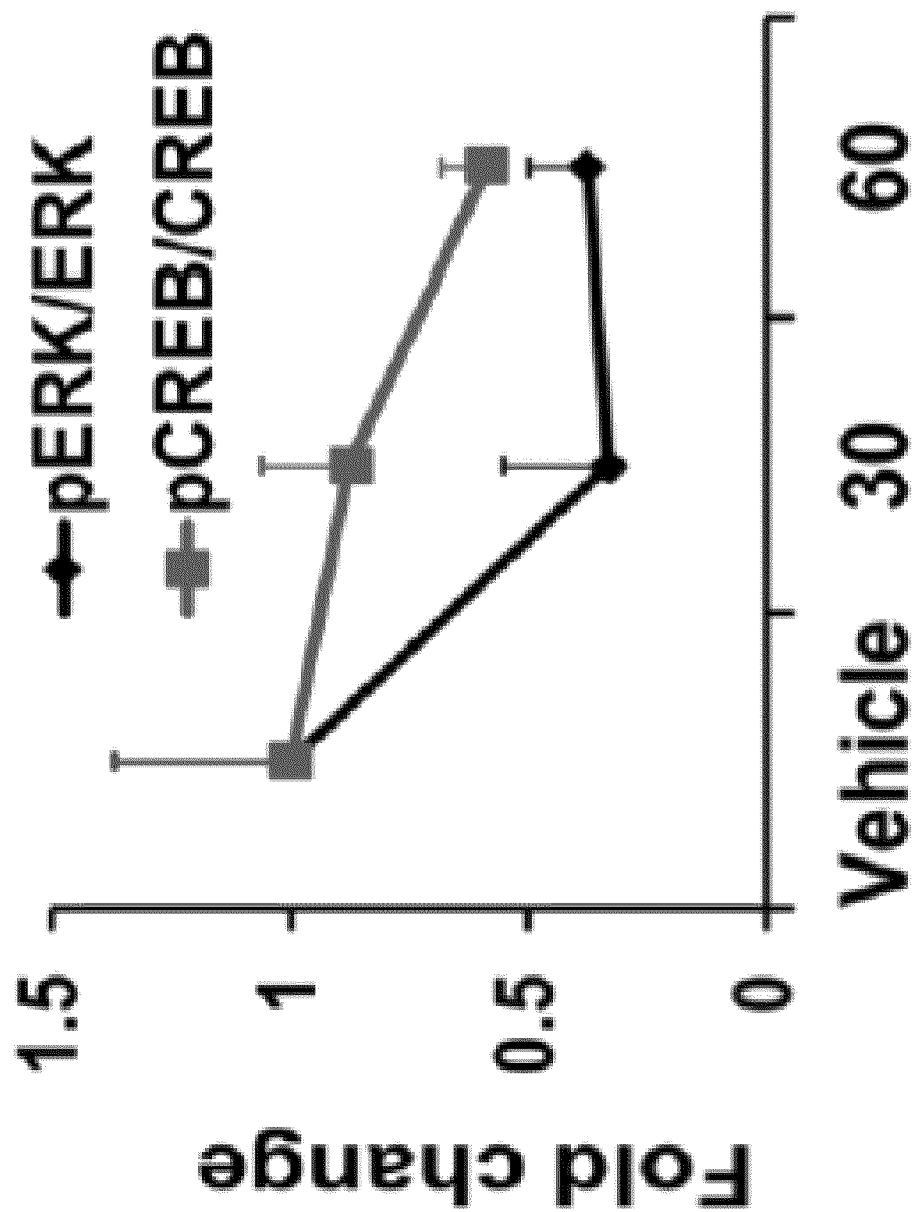
FIG. 14 provides the relative change in pERK/ERK and pCREB/CREB levels for mice treated with vehicle, 30 mg/kg OPC31260, or 60 mg/kg OPC31260, according to the working examples.
Figure 15:
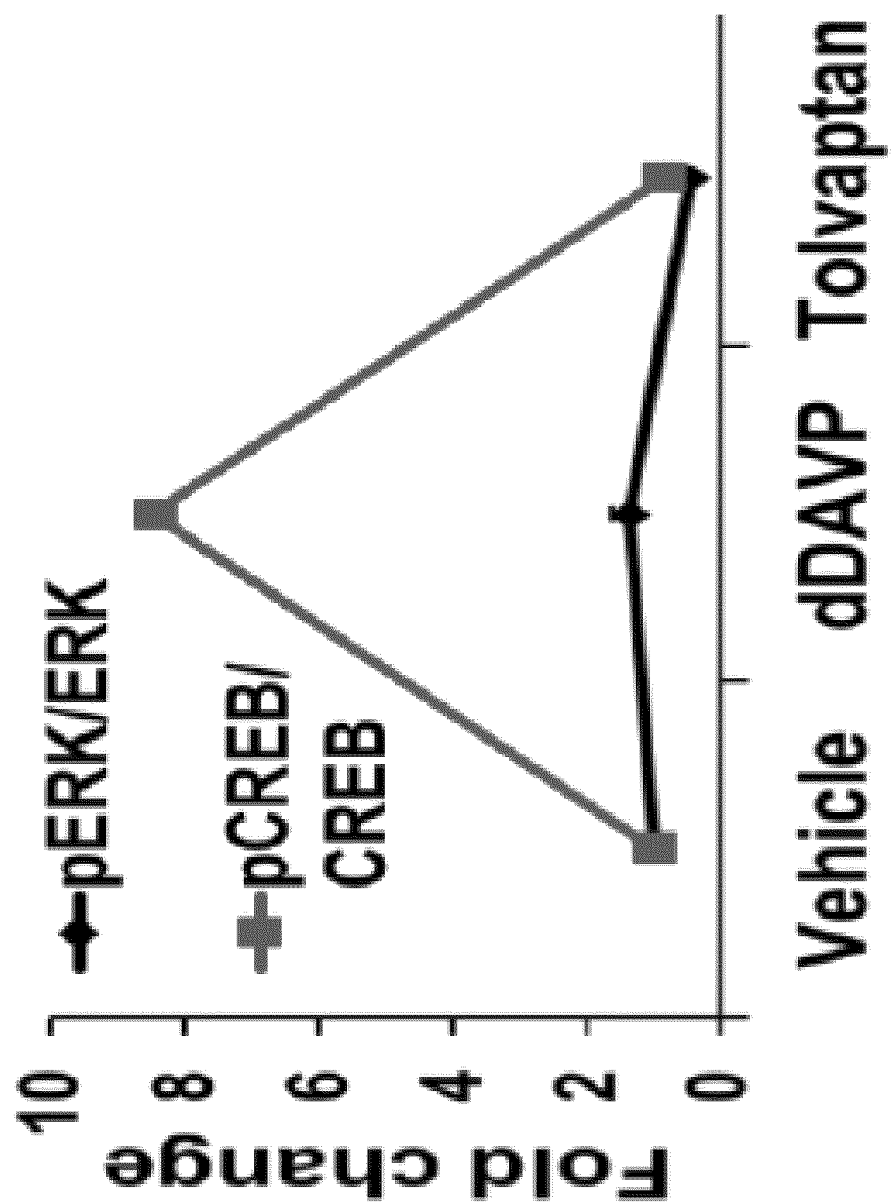
FIG. 15 provides the relative change in pERK/ERK and pCREB/CREB levels for mice treated with vehicle, dDAVP, or tolvaptan, according to the working examples.
Figure 16:
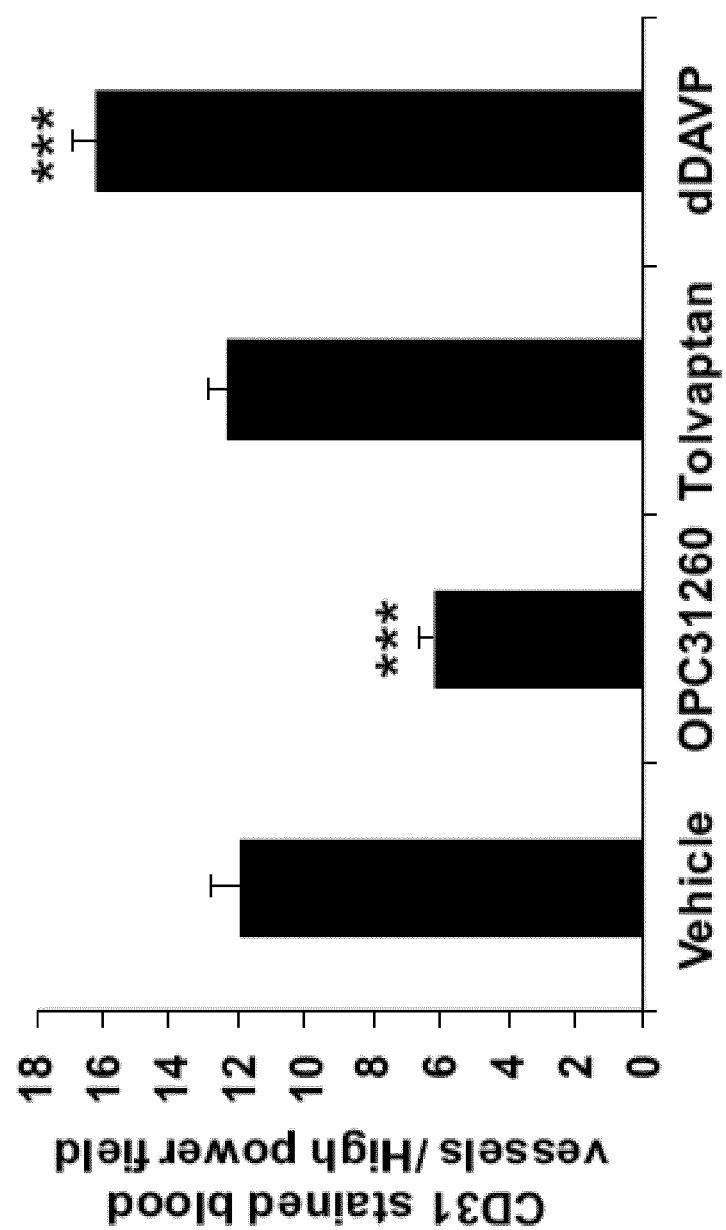
FIG. 16 provides the tumor micro-vessel density for CD31 stained vessels of tumors from mice treated with vehicle, OPC31260, tolvaptan, or dDAVP (***P<0.001 vs vehicle), according to the working examples.
Figure 17:
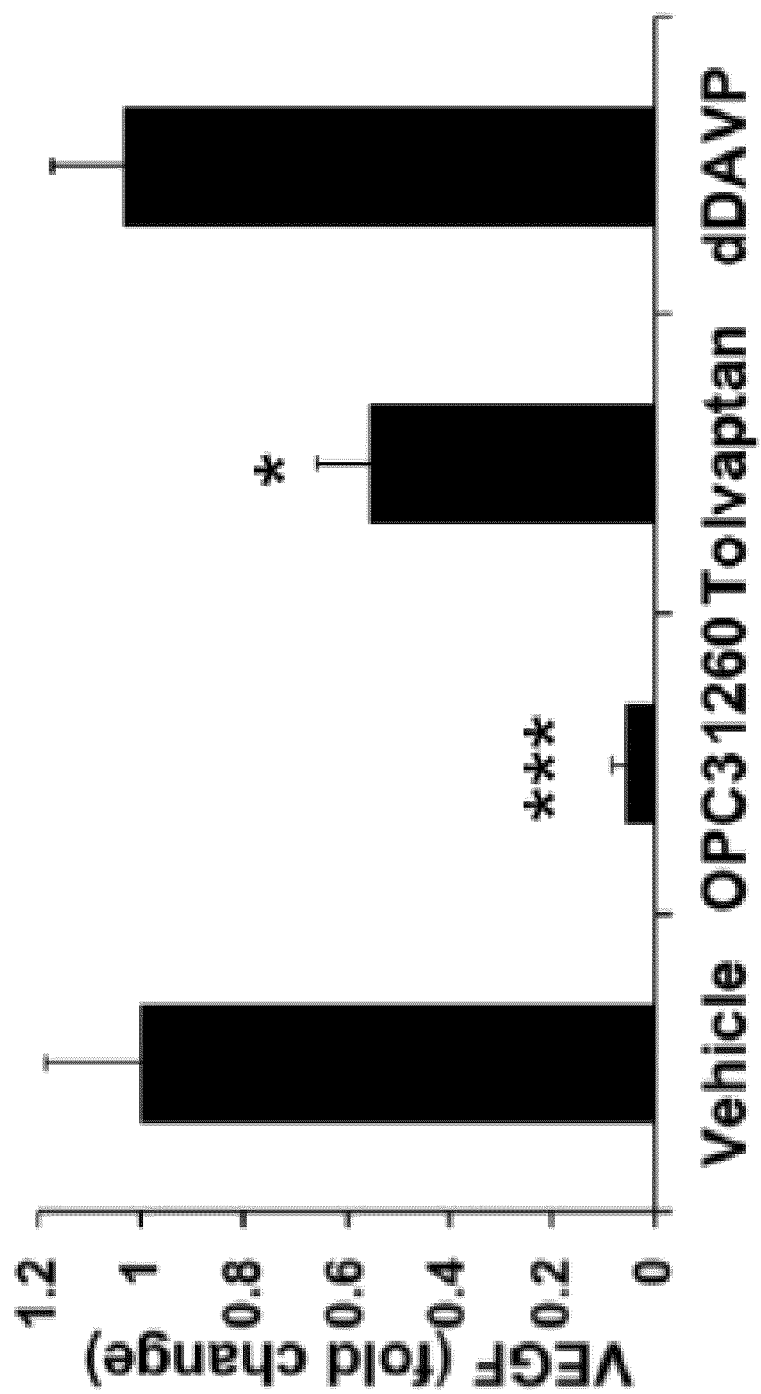
FIG. 17 provides the relative change in VEGF levels for tumors from mice treated with vehicle, OPC31260, tolvaptan, or dDAVP (***P<0.001 vs vehicle), according to the working examples.

To demonstrate target engagement, immunoblotting of tumor lysates was performed and reduced pERK1/2, pCREB and CREB levels in the OPC31260 and tolvaptan groups (FIGS. 14-15) was seen. In the dDAVP group, pCREB levels increased as expected. However, pERK1/2 and ERK1/2 levels were reduced (FIG. 15). pERK1/2 levels did not appear to increase in the dDAVP treatment group, the decreased pERK1/2 and pCREB levels in OPC31260 and tolvaptan treatment groups agree with their reduced cell proliferation. Both CREB and ERK1/2 are activated by $V_2R$ signaling via protein kinase-A (PKA) in the kidney[18, 19]. Moreover, CREB and ERK1/2 play a key role in cell proliferation, survival, and differentiation in multiple cancers types[20, 21]. Tumor micro-vessel density, determined by staining for CD31 was significantly reduced by OPC31260 treatment and increased by dDAVP treatment (FIG. 16). Tolvaptan treatment did not appear to alter tumor micro-vessel density. Since ERK1/2 regulates vascular endothelial growth factor (VEGF)[22], an important angiogenic growth factor, its expression in tumors was examined. OPC31260 and tolvaptan treatment significantly reduced VEGF protein levels compared to vehicle treatment, while dDAVP treatment did not affect VEGF levels (FIG. 17).

These results demonstrate a pathogenic role of AVP-$V_2R$ signaling in clear cell RCC, which is in stark contrast to its protective role in other cancers. Specifically, dDAVP treatment has been shown to reduce cell proliferation and tumor growth in breast, colon, lung and prostate cancers[7-9,23], metastasis in lung and colon cancer[23,24], and angiogenesis in breast cancer[7,9]. $V_2R$ antagonist therapy could hence enhance incipient growth of other tumor types. The pro-proliferative and tumor growth promoting effects of $V_2R$ stimulation in RCC is similar to what is seen in polycystic kidney disease (PKD), a disease characterized by the abnormal proliferation of renal tubular epithelial cells causing the progressive growth of renal cysts. Unlike clear cell RCC tumors, cysts in PKD originate mainly from collecting ducts[25] which naturally express $V_2R$. In PKD, $V_2R$ expression, and pERK1/2 mediated cell signaling are enhanced, stimulating increased cell proliferation[26], and $V_2R$ antagonists have been shown to slow cyst expansion[27]. Moreover, tolvaptan is currently in use for PKD therapy in many countries[28], and could be approved by the US FDA based on a recent clinical trial[29].

In summary, the $V_2R$ antagonists OPC31260 and tolvaptan were found to suppress tumor growth where such suppression appears to arise (at least in part) from reducing tumor cell proliferation, increasing apoptosis, and reducing angiogenesis in CCRCC. In contrast, the $V_2R$ agonist dDAVP increased cell proliferation, angiogenesis, and tumor growth in CCRCC.

Immunocompetent Animal Model

The Vh1$^{\Delta/\Delta}$Trp53$^{\Delta/\Delta}$Rb1$^{\Delta/\Delta}$ mice (Harlander S et al, *Nat Med* 2017 23(7):869-877) can spontaneously develop CCRCC. Gene deletion of Vhl and tumor suppressors p53 and Rb 1 will be achieved using a Ksp1.3-CreERT2, tamoxifen-inducible system. For the studies, 6-week old Vh1$^{\Delta/\Delta}$Trp53$^{\Delta/\Delta}$Rb1$^{\Delta/\Delta}$Ksp1.3-CreERT2 mice will be treated with vehicle (saline) or tamoxifen for 14 days used to obtain wildtype control mice and Vh1$^{\Delta/\Delta}$Trp53$^{\Delta/\Delta}$Rb1$^{\Delta/\Delta}$ mice with RCC stumors. Starting 30 weeks after start of tamoxifen, the wildtype and Vh1$^{\Delta/\Delta}$Trp53$^{\Delta/\Delta}$Rb1$^{\Delta/\Delta}$ mice will be treated with vehicle, dDAVP, OPC31260, or tolvaptan till 56 weeks. The effect of $V_2R$ activation or inhibition will be monitored by MRI as well as by gross and pathological analysis and of kidneys at sacrifice. We expect Vh1$^{\Delta/\Delta}$Trp53$^{\Delta/\Delta}$Rb1$^{\Delta/\Delta}$ mice treated with dDAVP to show increased tumor burden, while we expect OPC31260 and tolvaptan to significantly suppress tumor growth and (at certain concentrations) completely abolish tumor development.

REFERENCES

1. Boone, M, Deen, P M: Physiology and pathophysiology of the vasopressin-regulated renal water reabsorption. *Pflugers Archiv: European journal of physiology*, 456: 1005-1024, 2008.
2. Kaufmann, J E, Oksche, A, Wollheim, C B, Gunther, G, Rosenthal, W, Vischer, U M: Vasopressin-induced von Willebrand factor secretion from endothelial cells involves V2 receptors and cAMP. *The Journal of clinical investigation*, 106: 107-116, 2000.
3. Bolignano, D, Medici, M A, Coppolino, G, Sciortino, M T, Merlo, F M, Campo, S, Donato, V, Venuti, A, Sturiale, A, Zaccaria, D, Buemi, A, Lacquaniti, A, Buemi, M: Aquaretic inhibits renal cancer proliferation: Role of vasopressin receptor-2 (V2-R). *Urologic oncology*, 28: 642-647, 2010.
4. Heasley, L E: Autocrine and paracrine signaling through neuropeptide receptors in human cancer. *Oncogene*, 20: 1563-1569, 2001.
5. Keegan, B P, Akerman, B L, Pequeux, C, North, W G: Provasopressin expression by breast cancer cells: implications for growth and novel treatment strategies. *Breast Cancer Res Treat*, 95: 265-277, 2006.
6. North, W G: Gene regulation of vasopressin and vasopressin receptors in cancer. *Experimental physiology*, 85 Spec No: 27S-40S, 2000.
7. North, W G, Fay, M J, Du, J: MCF-7 breast cancer cells express normal forms of all vasopressin receptors plus an abnormal $V_2R$. *Peptides*, 20: 837-842, 1999.
8. North, W G, Fay, M J, Longo, K A, Du, J: Expression of all known vasopressin receptor subtypes by small cell tumors implies a multifaceted role for this neuropeptide. *Cancer research*, 58: 1866-1871, 1998.
9. Garona, J, Pifano, M, Orlando, U D, Pastrian, M B, Iannucci, N B, Ortega, H H, Podesta, E J, Gomez, D E, Ripoll, G V, Alonso, D F: The novel desmopressin analogue [V4Q5]dDAVP inhibits angiogenesis, tumour growth and metastases in vasopressin type 2 receptor-expressing breast cancer models. *International journal of oncology*, 46: 2335-2345, 2015.
10. Pifano, M, Garona, J, Capobianco, C S, Gonzalez, N, Alonso, D F, Ripoll, G V: Peptide Agonists of Vasopressin V2 Receptor Reduce Expression of Neuroendocrine Markers and Tumor Growth in Human Lung and Prostate Tumor Cells. *Front Oncol*, 7: 11, 2017.
11. Ripoll, G V, Garona, J, Pifano, M, Farina, H G, Gomez, D E, Alonso, D F: Reduction of tumor angiogenesis induced by desmopressin in a breast cancer model. *Breast Cancer Res Treat*, 142: 9-18, 2013.
12. Greef, B, Eisen, T: Medical treatment of renal cancer: new horizons. *British journal of cancer*, 115: 505-516, 2016.
13. Beksac, A T, Paulucci, D J, Blum, K A, Yadav, S S, Sfakianos, J P, Badani, K K: Heterogeneity in renal cell carcinoma. *Urologic oncology*, 35: 507-515, 2017.

14. Shen, S S, Krishna, B, Chirala, R, Amato, R J, Truong, L D: Kidney-specific cadherin, a specific marker for the distal portion of the nephron and related renal neoplasms. *Modern pathology: an official journal of the United States and Canadian Academy of Pathology, Inc,* 18: 933-940, 2005.
15. Kakade, V R, Tao, S, Rajagopal, M, Zhou, X, Li, X, Yu, A S, Calvet, J P, Pandey, P, Rao, R: A cAMP and CREB-mediated feed-forward mechanism regulates GSK3beta in polycystic kidney disease. *Journal of molecular cell biology,* 8:464-476, 2016.
16. Mayr, B, Montminy, M: Transcriptional regulation by the phosphorylation-dependent factor CREB. *Nat Rev Mol Cell Biol,* 2: 599-609, 2001.
17. Ryan, M B, Der, C J, Wang-Gillam, A, Cox, A D: Targeting RAS-mutant cancers: is ERK the key? *Trends Cancer,* 1: 183-198, 2015.
18. Steven, A, Seliger, B: Control of CREB expression in tumors: from molecular mechanisms and signal transduction pathways to therapeutic target. *Oncotarget,* 7: 35454-35465, 2016.
19. Pequeux, C, Keegan, B P, Hagelstein, M T, Geenen, V, Legros, J J, North, W G: Oxytocin- and vasopressin-induced growth of human small-cell lung cancer is mediated by the mitogen-activated protein kinase pathway. *Endocr Relat Cancer,* 11: 871-885, 2004.
20. Yamamura, Y, Ogawa, H, Yamashita, H, Chihara, T, Miyamoto, H, Nakamura, S, Onogawa, T, Yamashita, T, Hosokawa, T, Mori, T, et al.: Characterization of a novel aquaretic agent, OPC-31260, as an orally effective, nonpeptide vasopressin V2 receptor antagonist. *British journal of pharmacology,* 105: 787-791, 1992.
21. Kondo, K, Ogawa, H, Yamashita, H, Miyamoto, H, Tanaka, M, Nakaya, K, Kitano, K, Yamamura, Y, Nakamura, S, Onogawa, T, Mori, T, Tominaga, M: 7-Chloro-5-hydroxy-1-[2-methyl-4-(2-methylbenzoyl-amino)benzoyl]-2,3,4,5-tetrahydro-1H-1-benzazepine (OPC-41061): a potent, orally active nonpeptide arginine vasopressin V2 receptor antagonist. *Bioorg Med Chem,* 7: 1743-1754, 1999.
22. Berl, T, Quittnat-Pelletier, F, Verbalis, J G, Schrier, R W, Bichet, D G, Ouyang, J, Czerwiec, F S: Oral tolvaptan is safe and effective in chronic hyponatremia. *Journal of the American Society of Nephrology: JASN,* 21: 705-712, 2010.
23. Yang, L, Besschetnova, T Y, Brooks, C R, Shah, J V, Bonventre, J V: Epithelial cell cycle arrest in G2/M mediates kidney fibrosis after injury. *Nature medicine,* 16: 535-543, 531p following 143, 2010.
24. Carmeliet, P, Jain, R K: Angiogenesis in cancer and other diseases. *Nature,* 407: 249-257, 2000.
25. Ripoll, G V, Garona, J, Hermo, G A, Gomez, D E, Alonso, D F: Effects of the synthetic vasopressin analog desmopressin in a mouse model of colon cancer. *Anticancer Res,* 30: 5049-5054, 2010.
26. Ripoll, G V, Farina, H G, Yoshiji, H, Gomez, D E, Alonso, D F: Desmopressin reduces melanoma lung metastasis in transgenic mice overexpressing tissue inhibitor of metalloproteinases-1. *In Vivo,* 20: 881-885, 2006.
27. Tao, S, Kakade, V R, Woodgett, J R, Pandey, P, Suderman, E D, Rajagopal, M, Rao, R: Glycogen synthase kinase-3beta promotes cyst expansion in polycystic kidney disease. *Kidney international,* 87: 1164-1175, 2015.
28. Tones, V E: Vasopressin antagonists in polycystic kidney disease. *Kidney international,* 68: 2405-2418, 2005.
29. Tones, V E, Wang, X, Qian, Q, Somlo, S, Harris, P C, Gattone, V H, 2nd: Effective treatment of an orthologous model of autosomal dominant polycystic kidney disease. *Nature medicine,* 10: 363-364, 2004.
30. Gansevoort, R T, Arici, M, Benzing, T, Birn, H, Capasso, G, Covic, A, Devuyst, O, Drechsler, C, Eckardt, K U, Emma, F, Knebelmann, B, Le Meur, Y, Massy, Z A, Ong, A C, Ortiz, A, Schaefer, F, Torra, R, Vanholder, R, Wiecek, A, Zoccali, C, Van Biesen, W: Recommendations for the use of tolvaptan in autosomal dominant polycystic kidney disease: a position statement on behalf of the ERA-EDTA Working Groups on Inherited Kidney Disorders and European Renal Best Practice. *Nephrology, dialysis, transplantation: official publication of the European Dialysis and Transplant Association—European Renal Association,* 31: 337-348, 2016.
31. Shoaf, S E, Kim, S R, Bricmont, P, Mallikaarjun, S: Pharmacokinetics and pharmacodynamics of single-dose oral tolvaptan in fasted and non-fasted states in healthy Caucasian and Japanese male subjects. *Eur J Clin Pharmacol,* 68: 1595-1603, 2012.
32. Yamamura, Y, Nakamura, S, Itoh, S, Hirano, T, Onogawa, T, Yamashita, T, Yamada, Y, Tsujimae, K, Aoyama, M, 1. Boone, M, Deen, P M: Physiology and pathophysiology of the vasopressin-regulated renal water reabsorption. *Pflugers Archiv: European journal of physiology,* 456: 1005-1024, 2008.
33. Tao, S, Kakade, V R, Woodgett, J R, Pandey, P, Suderman, E D, Rajagopal, M, Rao, R: Glacogen synthase kinase-3beta promotes cyst expansion in polycystic kidney disease. *Kidney international,* 87: 1164-1175, 2015. Kotosai, K, Ogawa, H, Yamashita, H, Kondo, K, Tominaga, M, Tsujimoto, G, Mori, T: OPC-41061, a highly potent human vasopressin V2-receptor antagonist: pharmacological profile and aquaretic effect by single and multiple oral dosing in rats. *The Journal of pharmacology and experimental therapeutics,* 287: 860-867, 1998.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A method of treating a subject suffering from clear cell renal cell carcinoma, the method comprising
administering to the subject an effective amount of a compound selected from OPC31260, OPC41061, a pharmaceutically acceptable salt of either thereof, or a mixture of any two or more thereof;
wherein the effective amount is an amount effective for treating clear cell renal cell carcinoma.

B. The method of Paragraph A, further comprising administering water to the subject.

C. The method of Paragraph A or Paragraph B, wherein the administration comprises oral administration or parenteral administration.

D. The method of any one of Paragraphs A-C, wherein the administration comprises at least one of subcutaneous administration, intramuscular administration, intravenous administration, intraperitoneal administration, and oral administration.

E. The method of any one of Paragraphs A-D, wherein the subject is a human, a bovine, an equine, a canine, a feline, a simian, a porcine, an ovine, an avian, or a rodent (e.g., mouse).

F. The method of any one of Paragraphs A-E, wherein the subject is a human.

G. The method of any one of Paragraphs A-F, wherein the clear cell renal cell carcinoma comprises one or more of VHL mutant clear cell renal cell carcinoma and VHL wildtype clear cell renal cell carcinoma.

H. The method of any one of Paragraphs A-G, wherein the method comprises administering to the subject about 1 mg to about 150 mg of the compound per kilogram of the subject.

I. The method of any one of Paragraphs A-H, wherein the method comprises administering the compound to the subject from about 1 to about 7 times per week.

J. The method of any one of Paragraphs A-I, wherein a pharmaceutical composition comprises the compound and a pharmaceutically acceptable carrier.

K. The method of Paragraph J, wherein the pharmaceutical composition is formulated for oral administration or parenteral administration.

L. The method of Paragraph J or Paragraph K, wherein the pharmaceutical composition is formulated for at least one of subcutaneous administration, intramuscular administration, intravenous administration, intraperitoneal administration, and oral administration.

M. Use of OPC31260, OPC41061, a pharmaceutically acceptable salt of either thereof, or a mixture thereof or a composition comprising OPC31260, OPC41061, a pharmaceutically acceptable salt of either thereof, or a mixture thereof and a pharmaceutically acceptable carrier for treating a subject suffering from clear cell renal cell carcinoma.

N. Use of an effective amount of OPC31260, OPC41061, a pharmaceutically acceptable salt of either thereof, or a mixture thereof or a composition comprising an effective amount of OPC31260, OPC41061, a pharmaceutically acceptable salt of either thereof, or a mixture thereof and a pharmaceutically acceptable carrier for treating a subject suffering from clear cell renal cell carcinoma.

O. The use of Paragraph M or Paragraph N, wherein the treating comprises oral administration or parenteral administration.

P. The use of any one of Paragraphs M-O, wherein the treating comprises at least one of subcutaneous administration, intramuscular administration, intravenous administration, intraperitoneal administration, and oral administration.

Q. The use of any one of Paragraphs M-P, wherein the subject is a human, a bovine, an equine, a canine, a feline, a simian, a porcine, an ovine, an avian, or a rodent (e.g., mouse).

R. The use of any one of Paragraphs M-Q, wherein the subject is a human.

S. The use of any one of Paragraphs M-R, wherein the clear cell renal cell carcinoma comprises one or more of VHL mutant clear cell renal cell carcinoma and VHL wildtype clear cell renal cell carcinoma.

T. The use of any one of Paragraphs M-S, wherein the method comprises administering to the subject about 1 mg to about 150 mg of the compound per kilogram of the subject.

U. The use of any one of Paragraphs M-T, wherein the method comprises administering the compound to the subject from about 1 to about 7 times per week.

V. Use of OPC31260, OPC41061, a pharmaceutically acceptable salt of either thereof, or a mixture thereof in the manufacture of a medicament for the treatment of clear cell renal cell carcinoma in a subject.

W. The use of Paragraph V, wherein the medicament comprises an effective amount of OPC31260, OPC41061, the pharmaceutically acceptable salt of either thereof, or the mixture thereof.

X. The use of Paragraph V or Paragraph W, wherein the medicament is formulated for oral administration or parenteral administration.

Y. The use of any one of Paragraphs V-X, wherein the medicament is formulated for at least one of subcutaneous administration, intramuscular administration, intravenous administration, intraperitoneal administration, and oral administration.

Other embodiments are set forth in the following claims, along with the full scope of equivalents to which such claims are entitled.

What is claimed is:

1. A method of treating a subject suffering from clear cell renal cell carcinoma, the method comprising
    administering to the subject an effective amount of a compound selected from OPC31260, OPC41061, a pharmaceutically acceptable salt of either thereof, or a mixture of any two or more thereof;
    wherein the effective amount is an amount effective for treating clear cell renal cell carcinoma.

2. The method of claim 1, wherein the administration comprises oral administration or parenteral administration.

3. The method of claim 1, wherein the administration comprises at least one of subcutaneous administration, intramuscular administration, intravenous administration, intraperitoneal administration, and oral administration.

4. The method of claim 1, wherein the subject is a human, a bovine, an equine, a canine, a feline, a simian, a porcine, an ovine, an avian, or a rodent.

5. The method of claim 1, wherein the subject is a human.

6. The method of claim 1, wherein the method comprises administering to the subject about 1 mg to about 150 mg of the compound per kilogram of the subject.

7. The method of claim 1, wherein the method comprises administering the compound to the subject from about 1 to about 7 times per week.

8. The method of claim 1, wherein a pharmaceutical composition comprises the compound and a pharmaceutically acceptable carrier.

9. The method of claim 8, wherein the pharmaceutical composition is formulated for oral administration or parenteral administration.

10. The method of claim 8, wherein the pharmaceutical composition is formulated for at least one of subcutaneous administration, intramuscular administration, intravenous administration, intraperitoneal administration, and oral administration.

11. The method of claim 1, wherein the clear cell renal cell carcinoma comprises one or more of VHL mutant clear cell renal cell carcinoma and VHL wildtype clear cell renal cell carcinoma.

12. The method of claim 2, wherein the clear cell renal cell carcinoma comprises one or more of VHL mutant clear cell renal cell carcinoma and VHL wildtype clear cell renal cell carcinoma.

13. The method of claim 3, wherein the clear cell renal cell carcinoma comprises one or more of VHL mutant clear cell renal cell carcinoma and VHL wildtype clear cell renal cell carcinoma.

14. The method of claim 4, wherein the clear cell renal cell carcinoma comprises one or more of VHL mutant clear cell renal cell carcinoma and VHL wildtype clear cell renal cell carcinoma.

15. The method of claim 5, wherein the clear cell renal cell carcinoma comprises one or more of VHL mutant clear cell renal cell carcinoma and VHL wildtype clear cell renal cell carcinoma.

16. The method of claim 6, wherein the clear cell renal cell carcinoma comprises one or more of VHL mutant clear cell renal cell carcinoma and VHL wildtype clear cell renal cell carcinoma.

17. The method of claim 7, wherein the clear cell renal cell carcinoma comprises one or more of VHL mutant clear cell renal cell carcinoma and VHL wildtype clear cell renal cell carcinoma.

18. The method of claim 8, wherein the clear cell renal cell carcinoma comprises one or more of VHL mutant clear cell renal cell carcinoma and VHL wildtype clear cell renal cell carcinoma.

19. The method of claim 9, wherein the clear cell renal cell carcinoma comprises one or more of VHL mutant clear cell renal cell carcinoma and VHL wildtype clear cell renal cell carcinoma.

20. The method of claim 10, wherein the clear cell renal cell carcinoma comprises one or more of VHL mutant clear cell renal cell carcinoma and VHL wildtype clear cell renal cell carcinoma.

* * * * *